US006410241B1

(12) United States Patent
Sykes et al.

(10) Patent No.: US 6,410,241 B1
(45) Date of Patent: Jun. 25, 2002

(54) METHODS OF SCREENING OPEN READING FRAMES TO DETERMINE WHETHER THEY ENCODE POLYPEPTIDES WITH AN ABILITY TO GENERATE AN IMMUNE RESPONSE

(75) Inventors: Kathryn F. Sykes; Stephen Albert Johnston, both of Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/535,366

(22) Filed: Mar. 24, 2000

Related U.S. Application Data

(60) Provisional application No. 60/125,864, filed on Mar. 24, 1999, and provisional application No. 60/127,222, filed on Mar. 31, 1999.

(51) Int. Cl.$^7$ ................................................ C12Q 1/68
(52) U.S. Cl. ......................................... 435/6; 435/7.21
(58) Field of Search ........................... 435/6, 7.1, 325, 435/7.21; 514/44

(56) References Cited

U.S. PATENT DOCUMENTS

| | | | |
|---|---|---|---|
| 5,703,057 A | * | 12/1997 | Johnston et al. |
| 6,001,590 A | | 12/1999 | Komeda et al. ............ 435/69.1 |
| 6,143,530 A | | 11/2000 | Crouzet et al. ........... 435/91.42 |
| 6,280,977 B1 | * | 8/2001 | Liang et al. |

FOREIGN PATENT DOCUMENTS

| | | | |
|---|---|---|---|
| EP | 220482 | | 5/1987 |
| WO | WO 92/08798 | | 5/1992 |
| WO | WO 93/24639 | | 12/1993 |
| WO | WO 96/26270 | | 8/1996 |
| WO | WO 97/10345 | | 3/1997 |
| WO | WO 98/21322 | * | 5/1998 |
| WO | WO 98/38296 | | 9/1998 |
| WO | WO 99/02671 | | 1/1999 |
| WO | WO 99/45130 | | 9/1999 |
| WO | WO 99/66053 | | 12/1999 |
| WO | WO 0056914 | | 9/2000 |

OTHER PUBLICATIONS

Li et al (1997) Gene Therapy 4:449–454.*
Johnston et al (1997) Vaccine 15: 808–809.*
Barry et al (1995) Nature 377: 632–635.*
Logel et al., "Synthesis of crna probes from pcr–generated dna," *Biotechniques*, 13:604–610, 1992.
Cassata et al., "Rapid expression screening of *Caenorhabditis elegans* homeobox open reading frames using a two–step polymerase chain reaction promoter–gfp reporter contstruction technique," *Gene*, 212:127–135, 1998.
Johnston and Barry, "Genetic to genomic vaccination," *Vaccine*, 15:808–809, 1997.
Kain et al., "Universal promoter for gene expression without cloning: Expression–PCR," *Biotechniques*, 10:366–368, 370, 371, 372, 374, 1991.

Nisson et al., "Rapid and efficient cloning of Alu–PCR products using uracil DNA glycosylase," *PCR Methods Appl.*, 1:120–123, 1991.
Rashtchian et al., "Uracil DNA glycosylase–mediated cloning of polymerase chain reaction–amplified DNA: Application to genomic and cDNA cloning," *Anal. Biochem*, 206:91–97, 1992.
Switzer et al., "Rapid screening of open reading frames by protein synthesis with an in vitro transcription and translation assay," *Biotechniques*, 18:244–248, 1995.
Aslanidis and Jong, "Ligation–independent cloning of PCR products (LIC–PCR)," *Nucl. Acids Res.*, 18:6069–6074, 1990.
Aslanidis et al., "Minimal length requirement of the single–stranded tails for ligation–independent cloning (LIC) of pcr products," *PCR Methods and Applications*, 4:172–177, 1994.
Bolen et al., "Isolation and sequence analysis of a gene from the linear DNA plasmid pPacl–2 of pichia acaciae that shows similarity to a killer toxin gene of *Kluyveromyces lactis*," *Yeast*, 10:403–414, 1994.
Buttrick et al., "Behavior of genes directly injected into the rat heart in vivo," *Circulation Res.*, 70:193–198, 1992.
Carlyon et al., "Analysis of the organization of multicopy linear– and circular–plasmid–carried open reading frames in *Borrelia burgdorferi sensu lato* isolates," *Infect. Immun.*, 66:1149–1158, 1998.
Court and Bertrand, "Expression of the open reading frames of a senescence–inducing, linear mitochondrial plasmid of *Neurospora crassa*," *Plasmid*, 30:51–66, 1993.
Felgner and Liang, "Debugging expression screening," *Nature Biotech.*, 17:329–330, 1999.
Griffiths and Yang, "Recombination between heterologous linear and circular mitochondrial plasmids in the fungus Neurospora," *Mol. Gen. Genet*, 249:25–36, 1995.
Grzeszik et al., "Genes encoding the NAD–reducing hydrogenase of *Rhodococcus opacus* MR11," *Microbiology*, 143:1271–1286, 1997.
Gusew et al., "Linear DNA must have free ends to transform rat cells efficiently," *Mol. Gen. Genet.*, 206:121–125, 1987.

(List continued on next page.)

*Primary Examiner*—Remy Yucel
*Assistant Examiner*—Bronwen M. Loeb
(74) *Attorney, Agent, or Firm*—Fulbright & Jaworski L.L.P.

(57) ABSTRACT

The present invention relates to linear expression elements (LEEs) and circular expression elements (CEEs), which are useful in a variety of molecular biology protocols. Specifically, the invention relates to the use of LEEs and CEEs to screen for gene function, biological effects of gene function, antigens, and promoter function. The invention also provides methods of producing proteins, antibodies, antigens, and vaccines. Also, the invention relates to methods of making LEEs and CEEs, and LEEs and CEEs produced by such methods.

28 Claims, 8 Drawing Sheets

OTHER PUBLICATIONS

Haun and Moss, "Ligation–independent cloning of gluthathione S–transferase fusion genes for expression in *Escherichia coli,*" *Gene*, 112:37–43, 1992.

Haun et al., "Rapid, reliable ligation–independent cloning of pcr products using modified plasmid vectors," *Biotechniques*, 13:515–518, 1992.

Kaluz and Flint, "Ligation–independent cloning of PCR products with primers containing nonbase residues," *Nucl. Acids Res.*, 22:4845, 1994.

Kamper et al., "Heterologous gene expression on the linear DNA killer plasmid from *Kluyveromyces lactis*," *Curr. Genet.*, 19:109–118, 1991.

La Flamme et al., "Trypanosoma cruzi: expression of interleukin–2 utilizing both supercoiled plasmids and linear DNA's," *Exp. Parasitol.*, 83:159–163, 1996.

Lobocka et al, "Characterization of the primary immunity region of the *Escherichia coli* linear plasmid prophage N15," *J. Bacteriol.*, 178:2902–2910, 1996.

Mead et al., "A universal method for the direct cloning of PCR amplified nucleic acid," *Biotechnology*, 9:657–663, 1991.

Meinhardt et al., "A novel approach to express a heterologous gene *Kluyveromyces lactis* linear killer plasmids: expression of the bacterial APH gene from a cytoplasmic promoter fragment without in–phase fusion to the plasmid open reading frame," *Plasmid.*, 32:318–327, 1994.

Monoco et al., "Expression of recombinant human granulocyte colony–stimulating factor in CHO dhfr–cells: new insights into the in vitro amplification expression system," *Gene*, 180:145–150, 1996.

Rashtchian, "Novel methods for cloning and engineering genes using the polymerase chain reaction," *Curr. Opin. Biotech.*, 6:30–36, 1995.

Sampath et al., "Versatile vectors for direct cloning and ligation–independent cloning of PCR–amplified fragments for surface displays on filamentous bacteriophages," *Gene*, 190:5–10, 1997.

Schickel et al., "*Kluyveromyces lactis* killer system: analysis of cytoplasmic promoters of the linear plasmids," *Nucleic. Acids Res.*, 24:1879–1886, 1996.

Schründer and Meinhardt, "An extranuclear expression system for analysis of cytoplasmic promoters of yeast linear killer plasmids," *Plasmid*, 33:139–151, 1995.

Schünder et al., "Extranuclear expression of the bacterial xylose isomerase (xylA) and the UDP–glucose deydrogenase (hasB) genes in yeast with *Kluyveromyces lactis* linear killer plasmids as vectors," *Curr. Microbiol.*, 33:323–330, 1996.

Sekine et al., "Identification and characterization of the linear IS3 molecules generated by staggered breaks," *J. Biol. Chem.*, 271:197–202, 1996.

Sykes and Johnston, "Linear expression elements: a rapid, in vivo, method to screen for gene functions," *Nat. Biotech.*, 17:355–359, 1999.

Tang et al., "Genetic immunization is a simple method for eliciting an immune response," *Nature*, 356:152–154, 1992, only pages 152 and 153 provided.

Tanguy–Rougeau et al., "Expression of a foreign $Km^R$ gene in linear killer DNA plasmids in yeast," *Gene.*, 91:43–50, 1990.

Ton–Hoang et al., "Efficient transportation of IS911 circles in vitro," *Embo. J.*, 17:1169–1181, 1998.

Turner and Moyer, "A PCR–based method for manipulation of the Vaccinia virus genome that eliminates the need for cloning," *Bio Techniques*, 13:764–771, 1992.

Xie and Tsong, "Study of mechanisms of electric field–induced DNA transfection V. effects of DNA topology on surface binding, cell uptake, expression, and integration into host chromosomes of DNA in the mammalian cell," *Biosphys. Jour.*, 65:1684–1689, 1993.

\* cited by examiner

SEQUENCE LISTING

```
<160> NUMBER OF SEQ ID NOS: 5

<210> SEQ ID NO 1
<211> LENGTH: 15
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 1
acuacuacua cuacu                                                      15

<210> SEQ ID NO 2
<211> LENGTH: 15
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 2
aguaguagua guagu                                                      15

<210> SEQ ID NO 3
<211> LENGTH: 14
<212> TYPE: RNA
<213> ORGANISM: Artificial Sequence
<220> FEATURE:
<223> OTHER INFORMATION: Description of Artificial Sequence: Synthetic
      Primer
```

-continued

```
<400> SEQUENCE: 3
augaugauga ugau                                                      14

<210> SEQ ID NO 4
<211> LENGTH: 15
<212> TYPE: RNA
<213> ORGANISM: Artificial Sequence
<220> FEATURE:
<223> OTHER INFORMATION: Description of Artificial  Sequence:  Synthetic
      Primer

<400> SEQUENCE: 4
acuacuacua cuacu                                                     15

<210> SEQ ID NO 5
<211> LENGTH: 14
<212> TYPE: RNA
<213> ORGANISM: Artificial Sequence
<220> FEATURE:
<223> OTHER INFORMATION: Description of Artificial  Sequence:  Synthetic
      Primer

<400> SEQUENCE: 5
aucaucauca ucau                                                      14
```

METHODS OF SCREENING OPEN READING FRAMES TO DETERMINE WHETHER THEY ENCODE POLYPEPTIDES WITH AN ABILITY TO GENERATE AN IMMUNE RESPONSE

This application claims the benefit of U.S. Provisional Application Ser. No. 60/125,864, filed Mar. 24, 1999, and U.S. Provisional Application Ser. No. 60/127,222, filed Mar. 31, 1999, each of which disclosures is specifically incorporated herein by reference in its entirety.

The government owns rights in the present invention pursuant to DARPA Federal grant number BAA 96-24.

BACKGROUND OF THE INVENTION

1. Field of the Invention

The present invention relates generally to the field of molecular biology and functional genomics. More particularly, it concerns methods to screen genes or gene components for their functions or biological effects and methods of generating immune responses or immune reagents.

2. Description of Related Art

Genomic sequencing efforts are producing a wealth of data. Sequence information is being compiled not only from humans but also plants, animals and microbes. This abundance of data has spawned the need for new technologies for analyzing and functionally assessing the millions of genes that will now be available. The expanding repertoire of areas that functional genomics are applied should lead to new insights into evolution, reveal how cellular pathways integrate, and yield new drugs and vaccines. A current challenge is to develop the technologies that will enable these advancements.

For example, there are currently at least thirty microbial genome sequences in the public domain and additional projects underway. Most of these are pathogens of humans or commercial animals. One often expressed hope is that knowledge of these sequences will lead to the development of vaccines against these pathogens. Though computational analyses may be useful, the more sure-footed approach would be to functionally screen each gene from all the pathogens in animals for its value as a protective agent. However the time and expense of cloning thousands of genes from each pathogen then preparing appropriate reagents from them is prohibitive, using current methods.

In order to quickly and effectively assess the activity of any particular gene product or a physiological response to it, an assay method is required that avoids plasmids and bacterial cloning procedures. This ideal method would also permit the plethora of new genes from sequencing projects to be rapid screened in organisms, cells or cell-free systems.

SUMMARY OF THE INVENTION

The inventors have determined methods and compositions which allow for the production of linear expression elements ("LEEs") and/or circular expression elements ("CEEs") encompassing a complete gene (promoter, coding sequence, and terminator). These LEEs and CEEs can be directly introduced into and expressed in cells or an intact organism to yield expression levels comparable to those from a standard supercoiled, replicative plasmid.

In some general embodiments, the invention relates to methods of assaying for the production or regulation of expression of at least one polypeptide from a linear or circular nucleic acid segment comprising a promoter or putative promoter and an ORF or putative ORF. These methods may comprise: a) obtaining at least one linear or circular nucleic acid segment comprising a promoter or putative promoter and an ORF encoding a peptide or putative ORF; b) placing the nucleic acid segment under conditions conducive to expression of the polypeptide from the ORF; and c) assaying for the production or regulation of expression of a polypeptide from the ORF or putative ORF. In many preferred embodiments, the nucleic acid segment will comprise a terminator. However, in some applications, including those where the linear nucleic acid segment is assayed in a cell-free expression system, no terminator is required. In some cases, the linear nucleic acid is obtained by a PCR® process. In other situations, the linear nucleic acid may be cut out of a plasmid, chromosome, or other larger piece of nucleic acid; in these cases, the linear nucleic acid cut from the larger piece of nucleic acid will typically comprise a promoter and ORF, and in many cases a terminator, that are already in operable relationship.

Of course, those of skill in the art will understand that the promoter or putative promoter and any terminator will typically be placed in a operable relationship to the ORF or putative ORF, employing methods disclosed herein or know to those in the art.

In many cases, the linear nucleic acid segment is obtained by synthesis. In some preferred methods, the synthesis comprises non-covalent linkage of the promoter to the ORF. For example, this non-covalent linkage may be performed by a) obtaining a PCR® product comprising the nucleic acid segment, which PCR® product is obtained by amplification from at least one primer that has complementary stretches comprising deoxyuridines with uracil-DNA glycosylase to create overhangs to which the promoter can link; b) providing the promoter; and c) non-covalently linking the promoter to the nucleic acid segment to create the linear or circular expression element. In many cases a terminator will be non-covalently linked to the ORF, using a similar technique, although it is possible that the ORF or putative ORF may have a terminator incorporated into it, such that the addition of a terminator may not be required. In some presently employed embodiments, the primer that has complementary stretches comprising deoxyuridines. These stretches allow the use of uracil-DNA glycosylase, or another suitable enzyme to create overhangs to which the promoter can non-covalently link create the linear or circular expression element. The non-covalent linkage of a terminator to the ORF can be accomplished by much the same technique. Of course, it will be understood to those of skill in the art that other nucleotide/enzyme pairs may be used to perform this non-covalent linking, and that other techniques of non-covalent linking may be employed, so long as the purposes of the invention are accomplished. In some specific embodiments, the primer comprises the promoter and the terminator in divergent orientation, such that the step of non-covalently linking the promoter and the terminator to the ORF results in a circular expression element.

While the promoter may be of any origin that will work for the purposes of the invention, in some preferred embodiments, the promoter is a eukaryotic promoter. Likewise, the terminator may be of any source, but in may cases the terminator will be a eukaryotic terminator.

The nucleic acid segment containing the ORF, putative ORF, or any other nucleic acid segment which is comprised in a LEE or CEE may be obtained from any of a variety of sources. For example, it may be obtained by PCR®, from a linear nucleic acid that is cut out of a plasmid, or obtained by synthesis.

In some methods according to the invention, the nucleic acid segment forming LEE or CEE is placed into a cell so that it is under conditions conducive to expression of a polypeptide from the ORF or putative ORF. In some preferred embodiments, the linear nucleic acid is placed into a cell but not integrated into the cell's genome. The inventors have determined that integration into the genome is not required for expression of linear nucleic acids. Further, the inventors have determined that supercoiled plasmids are not required for expression of genes. In some embodiments, the cell is in cell culture, while in others, the cell is comprised in a tissue or an entire organism. All organisms are contemplated in this regard, including, but not limited to plant, animal, mammal, fish, bird, reptilian, human, rabbit, rat, hamster, mouse and other cells. The LEEs and CEEs of the invention may be placed into cells using any of the technologies described elsewhere in the specification. In some preferred embodiments, a LEE or CEE in injected into the cell. In some particularly preferred embodiments injection comprises microprojectile bombardment. In other embodiments, the LEE or CEE many be placed in a cell-free expression reaction.

Various preferred embodiments relate to methods of analyzing a nucleic acid sequence comprising: a) obtaining a nucleic acid segment; b) linking the nucleic acid segment to a promoter and a terminator to create a linear or circular expression element; c) providing the linear or circular expression element to a cell-free expression system or to a cell under conditions conducive to expression of any product encoded for by the nucleic acid segment; and d) analyzing any expression of any product encoded by the nucleic acid sequence. The nucleic acid segments employed in these methods can be obtained in manners described above, and elsewhere in the specification. Likewise the linkage of the promoter and terminator may be non-covalent linkage, as described elsewhere. In some embodiments wherein the nucleic acid sequence comprises an ORF to be analyzed for function, for example, to determine whether the nucleic acid encodes a polypeptide. These methods also allow one to determine whether or not the ORF encodes an antigenic polypeptide, and/or to determine biological properties of the polypeptide. For example one can determine whether the linear or circular expression element, or an ORF contained therein, is suitable for use in a vaccine. An advantage of these methods is that more than one distinct nucleic acid segment is analyzed in a single procedure.

As discussed above, and elsewhere in this specification, the methods of the invention may involve assaying for expression of a polypeptide which may be encoded in an ORF or putative ORF. In some preferred embodiments, the methods comprise assaying for expression of the polypeptide; in some cases, such assaying includes identification of the polypeptide. Other embodiments may comprise assaying the expression of a reporter gene product encoded in the ORF.

Still other specific embodiments comprise assaying for function of the promoter. For example, the function of the promoter may be assayed by determining whether a reporter gene product encoded in the ORF is expressed. A reporter gene is a gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fluorometric, radioisotopic or spectrophotometric analysis of the cell culture. In some embodiments, the assessment of promoter function will comprise comparing the function of two or more putative promoters for which function is assayed. In this manner, the invention provides for an efficient manner of screening a variety of promoters for function in a specific system. For example, a library of promoters from a variety of sources can be assayed such that an optimal promoter for a particular system is determined. Alternatively, a variety of mutants of a specific promoter may be assayed to determine whether they have promoter activity. In order to perform such assays, one may construct a variety of linear nucleic acid segments, using standard molecular biology means, each of which comprises a putative promoter or a promoter and a polypeptide encoding a reporter gene. This variety of linear nucleic acids may then be introduced to a system that enables the assessment of their function by looking for expression of the reporter gene.

In addition to allowing for analysis of ORFs or putative ORFs, the invention provides methods of analyzing a nucleic acid segment for activity as a promoter comprising: a) obtaining a nucleic acid segment encoding a putative promoter; b) linking the nucleic acid segment encoding the putative promoter to a nucleic acid encoding a polypeptide to create a linear or circular expression element; c) providing the linear or circular expression element to a cell-free expression system or to a cell under conditions conducive to expression of the polypeptide; and d) analyzing any expression of the polypeptide. For example, the function of the promoter may be assayed by determining whether a reporter gene product encoded in the ORF is expressed. A reporter gene is a gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fluorometric, radioisotopic or spectrophotometric analysis of the cell culture. In some embodiments, the assessment of promoter function will comprise comparing the function of two or more putative promoters for which function is assayed. In this manner, the invention provides for an efficient manner of screening a variety of promoters for function in a specific system. For example, a library of promoters from a variety of sources can be assayed such that an optimal promoter for a particular system is determined. Alternatively, a variety of mutants of a specific promoter may be assayed to determine whether they have promoter activity. In order to perform such assays, one may construct a variety of linear nucleic acid segments, using standard molecular biology means, each of which comprises a putative promoter or a promoter and a polypeptide encoding a reporter gene. This variety of linear nucleic acids may then be introduced to a system that enables the assessment of their function by looking for expression of the reporter gene. In this manner, one is able to assay for function of the promoter or putative promoter, and determine whether the promoter or putative promoter is functioning, and the extent of any such function, by determining whether the reporter gene product encoded in an ORF is expressed. In some embodiments, the methods may be used to compare the function of two or more putative promoters. It is advantageous that more than one distinct nucleic acid segment encoding a putative promoter can analyzed in a single procedure. The nucleic acid encoding the putative promoter may be, for example, a native nucleic acid, prepared by mutation of a native promoter sequence, or prepared by chemical synthesis. One of skill can use this these techniques to test and optimize promoters or putative promoters from any source.

In additional embodiments, the invention relates to methods of screening for a biological response comprising: a) obtaining a linear or circular expression element by a process comprising: obtaining a DNA segment comprising an ORF; linking the ORF to a promoter and a terminator to create a linear or circular expression element; and b)providing the expression element to an organism under conditions conducive to expression of any product encoded for by the ORF. In such cases, more than one type of linear or circular expression element is introduced to the organism. These methods may encompass method of producing antibodies for analytical purposes, for example, when the biological function is to result in an immune response. In other embodiments, these methods may provide methods of vaccinating the organism, as described below.

In some specific embodiments, the invention allows for the vaccinating an organism comprising obtaining a linear or circular expression element by a process comprising obtaining a DNA segment comprising an ORF and linking the ORF to a promoter and a terminator to create a linear or circular expression element; and c) providing the expression element to an organism under conditions conducive to expression of any product encoded for by the ORF, such that immune response is produced in the animal. In such vaccines, more than one type of linear or circular expression element is introduced to the organism, in order to create a polyvalent vaccine that my be directed against more that one infectious agent, cancer, or other disease or against a variety of antigens from a single infectious agent, cancer, or other disease. For example, a plurality of types of linear or circular expression elements may introduced to the organism., and the plurality of types of linear or circular expression elements may comprise elements encoding distinct polypeptides of a pathogen. While those of skill in the art will realize that the pathogen may be of any form, in some preferred embodiments, the pathogen is a virus, bacterium, fungus, alga, protozoan, arthropod, nematode, platyhelminthe, or plant. In even more specific embodiments, the individual linear or circular expression elements encoding all potential allergens of a virus is comprised in the plurality of types of linear or circular expression elements. The ORF may also encodes a polypeptide which is useful for vaccination against cancer, or another disease, as known to those of skill in the art.

The invention also contemplates methods of selecting ORFs effective for generating an immune response specific to a pathogen, cancer, or other disease in an organism, comprising: a) preparing a plurality of linear or circular expression elements comprising a plurality of DNA segments comprising ORFs from a pathogen, cancer, or other disease; b) introducing the plurality of linear or circular expression elements into an organism; and c) selecting from the plurality of linear or circular expression elements ORFs that are effective to generate said immune response. Such methods may further comprising testing said organism against challenge with the pathogen wherein the organism is protected against challenge with the pathogen. In this manner, one or more antigens conferring a protective response may identified by screening of the organism.

The invention also relates to linear and circular expression element and method of producing linear and circular expression elements. For example, such methods may comprise a) obtaining a DNA segment comprising an ORF, putative ORF, or other sequence; and b) linking the DNA segment to a promoter and a terminator to create a linear or circular expression element. In some cases, the DNA segment is obtained from a process involving PCR®, and in some specific embodiments, the PCR® reaction is primed with oligonucleotides having a complementary stretch incorporating deoxyuridines. For example, the deoxyuridines may be incorporated every third position of the complementary stretch. The ORF may be non-covalently linked to the promoter and the terminator, and this non-covalent linkage may be performed as described elsewhere in this specification.

In some specific embodiments, the invention relates to linear or circular expression elements comprising a DNA segment comprising an ORF and a promoter and terminator non-covalently linked to said ORF. In other aspects, the invention relates to antibodies, antigens and vaccines that are prepared, assayed, or determined employing the above-described methods.

As used herein the specification, "a" or "an" may mean one or more. As used herein in the claim(s), when used in conjunction with the word comprising, the words "a" or "an" may mean one or more than one.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7A Gene-gun delivery of bi-LEE.LUC leads to similar gene expression with or without covalent linkage. FIG. 7B Needle delivery of the LEE can be improved by in vitro ligation. Note 100-fold difference in x-axis scale between ear ($\times 10^6$) and muscle ($\times 10^4$) sample readouts. Activities are reported as in FIG. 1. –lig= annealed but not ligated in vitro. +lig=treated with ligase 30 min before in vivo introduction. FIG. 7C. Liposome delivery of bi-LEE.LUC into WEH1 tissue culture cells leads to higher levels of luciferase activity than delivery of the LUC-encoding plasmid pCMV.LUC. The experiment was performed three times with lumen determinators measured in duplicate 18 hours after transfection (Superfect, Qiagen).

DESCRIPTION OF ILLUSTRATIVE EMBODIMENTS

Figure 1:
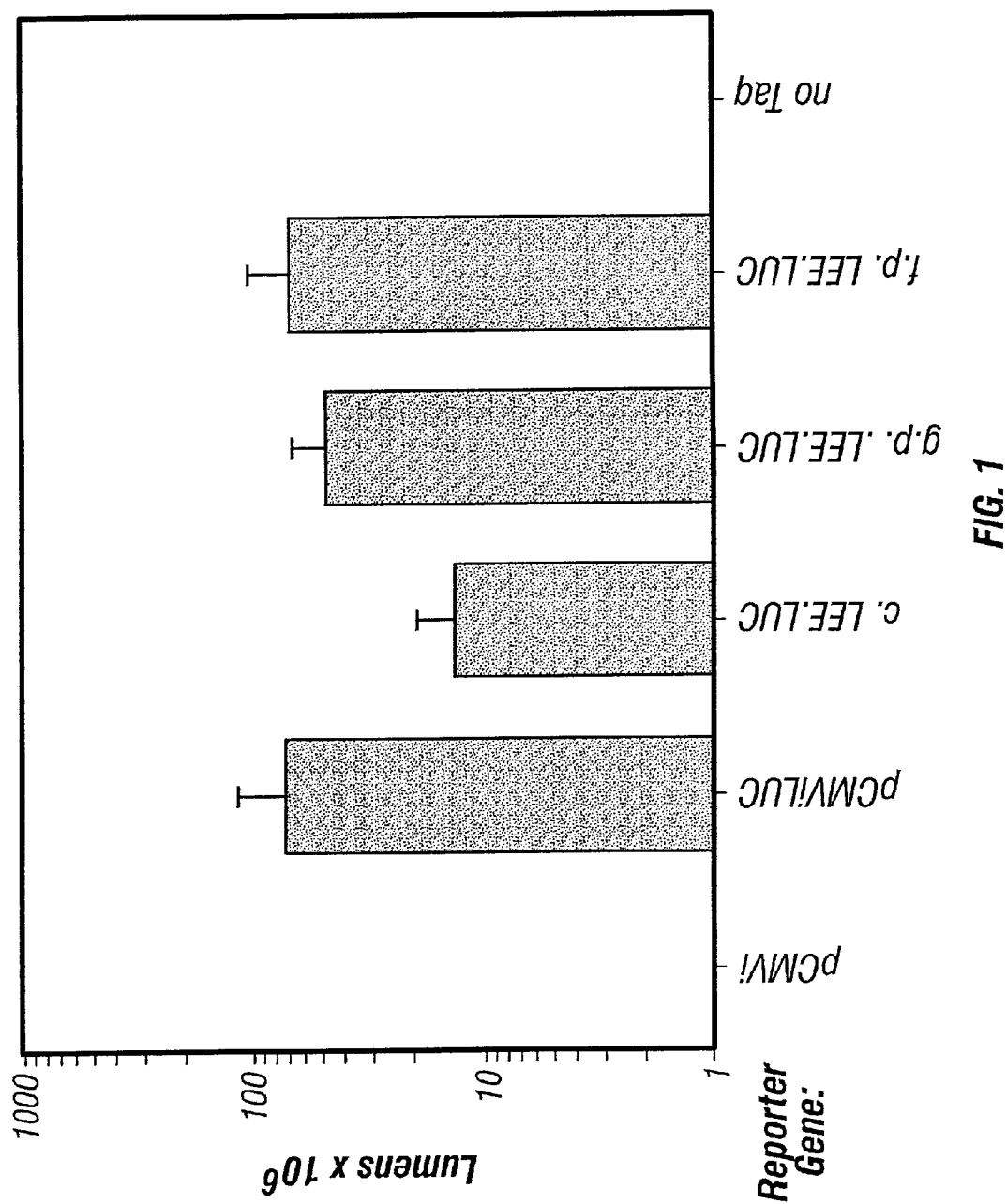
FIG. 1. Delivery and expression of a PCR®-amplified luciferase gene in mice. Ears were bombarded with empty plasmid, pCMVi (0.33 µg), luciferase plasmid, pCMViLUC (0.33 µg), or a molar-equivalent dose (0.17 µg) of a PCR® product encoding luciferase. c. LEE.LUC=crude product directly loaded onto microprojectiles; f.p. LEE.LUC=filter purified product; g.p. LEE.LUC agarose gel purified product; no Taq=filter-purified sample prepared without Taq polymerase. Activities are plotted as lumens×$10^6$ per 1.0 µg plasmid or per 0.5 µg PCR® product introduced into an ear. Lumens were measured from four or more bombarded ears then averaged. Standard errors are defined.

The increasing availability of genomic sequence information has accentuated the need for new methods to efficiently assess gene function and prepare reagents to study these functions. The disclosed methods and compositions of the invention allow any open-reading frame (ORF), for example, PCR® amplified ORFs, to be non-convalently linked to an eukaryotic promoter and terminator. These quickly linked fragments can be directly injected into animals to produce local gene expression. It has also been demonstrated that the ORFs can be injected into mice to produce antibodies to the encoded foreign protein by simply attaching mammalian promoter and terminator sequences. This technology makes it possible to rapidly screen large numbers of genes for their function in vivo or produce an immune response to them without the necessity of cloning, bacterial propagation or protein purification.

Preparation of genes for transfection and expression has become synonymous with the cloning, then amplification and purification of plasmid constructs from bacteria. The process involves many steps that consume time, money, and carries the bias, toxicity, and contamination risks inherent to bacterial propagation. The inventors' have developed a two-pronged strategy that streamlines these activities. In some embodiments, it is based on: 1) delivery of genetic expression units into organisms without the need of bacterial propagation and 2) cassette-like linkage of promoters, genes, and terminators. Efficient use of PCR® products, restriction fragments or chemically synthesized genes as vehicles of expression enables genetic constructs to be generated on a scale, purity, and time-frame that are not possible by usual cloning methods. This protocol has several other advantages. Since genes are produced without bacteria, problems associated with bacterial growth such as toxicity, lethality, or stability are avoided. In contrast to conventional cloning where an individual PCR® product is isolated in a plasmid and propagated, this method introduces the entire amplified sample thus avoiding concern that any particular PCR® product carries a mutation. This single-tube, bio-free protocol would be adaptable to robotic handling and high-through-put screens. Finally, the synthetic genes will maintain the advantage of unmethylated purines (CpGs) as adjuvant in raising immune responses (Sato et al., 1996).

This protocol will be useful in several manners. First, a genome database will allow oligos to be designed to amplify each of the genes of an organism. As shown in the examples below, dU residues and UDG enzymes were used to generate attachable sequences. While this was very effective, relatively high levels of reporter gene expression were also observed even without enzyme treatment. It may be that exposure to endogenous UDG enables in vivo annealing and sticky-end ligation. LEEs built from either two or three PCR® products generated similar levels of gene activity.

Each ORF can be generated, annealed to a promoter and terminator of choice, then directly introduced into a test cell, tissue or organims or used in a cell-free system. LEEs and CEEs can be screened individually or in pools. With this method, it is envisioned, for example, that all the genes of an organism can be introduced as genetic vaccines into organisms (e.g., an animal) in a matter of days. The animals can be subsequently challenged with pathogen to determine which genes protect against disease. Isolating individual LEEs or CEEs from protective pools can be conducted as previously described for plasmid libraries (Barry et al., 1995).

A second application is in developing immunological reagents. LEEs and CEEs can be used to produce antibodies to an ORF. Antibodies to all a pathogen's ORFs can be produced, then used to probe pathogen-infected tissue in immunolocalization analyses to elucidate which proteins are present at any pathogen stage-of-interest. Identified gene products are excellent vaccine candidates or drug targets. Alternatively, the antibodies could be screened for diagnostic or therapeutic value.

A third application is to screen for other physiological responses caused by expression of a gene product.

A fourth application of LEEs and CEEs is to screen for altered promoter function. Libraries of promoters containing deletions or mutations are linked to a reporter gene and introduced directly into the relevant animal/plant tissue or cell culture. For example, reporter activity can be used to monitor gene expression levels, cell-type specific expression, or responses to treatments such as drugs. Since this protocol allows an efficient and fast method to generate expression elements of any design for direct introduction into tissue, it is applicable to other applications.

A fifth application of LEEs and CEEs could be in cell-free expression systems. In vitro transcribed/translated LEEs and CEEs could be used to rapidly and systematically generate proteins encoded by any number of ORFs. The proteins could be screened for a function or activity of interest, for example, the ability to bind a drug or other protein target.

A. Promoters

In certain aspects of the present invention, a LEE or CEE that is employed will comprise at least one promoter. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence (ie., ORF) to control transcriptional initiation and/or expression of that sequence. A promoter may or may not be used in conjunction with an "enhancer," which refers to a cis-acting regulatory sequence involved in the transcriptional activation of a nucleic acid sequence.

Certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well. However, in certain embodiments a promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence.

Naturally, it will be important to employ a promoter and/or enhancer that effectively directs the expression of the DNA segment in the organelle, cell, tissue and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Tables 1 lists several elements/promoters that may be employed, in the context of the present invention, to regulate the expression of a gene. This list is not intended to be exhaustive of all the possible elements involved in the promotion of expression but, merely, to be exemplary thereof. Table 2 provides non-limiting examples of inducible elements, which are regions of a nucleic acid sequence that can be activated in response to a specific stimulus.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al., 1990 |

TABLE 1-continued

Promoter and/or Enhancer

| Promoter/Enhancer | References |
|---|---|
| Immunoglobulin Light Chain | Queen et al., 1983; Picard et al., 1984 |
| T-Cell Receptor | Luria et al., 1987; Winoto et al., 1989; Redondo et al., 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al., 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| T-Globin | Bodine et al., 1987; Perez-Stable et al., 1990 |
| β-Globin | Trudel et al., 1987 |
| C-fos | Cohen et al., 1987 |
| C-HA-ras | Triesman, 1986; Deschamps et al., 1985 |
| Insulin | Edlund et al., 1985 |
| Neural Cell Adhesion Molecule (NCAM) | Hirsh et al., 1990 |
| α₁-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984 a, b, 1988; |

TABLE 1-continued

Promoter and/or Enhancer

| Promoter/Enhancer | References |
|---|---|
| | Bosze et al., 1986; |
| | Miksicek et al., 1986; |
| | Celander et al., 1987; |
| | Thiesen et al., 1988; |
| | Celander et al., 1988; |
| | Chol et al., 1988; |
| | Reisman et al., 1989 |
| Papilloma Virus | Campo et al., 1983; |
| | Lusky et al., 1983; |
| | Spandidos and/or Wilkie, 1983; |
| | Spalholz et al., 1985; |
| | Lusky et al., 1986; |
| | Cripe et al., 1987; |
| | Gloss et al., 1987; |
| | Hirochika et al., 1987; |
| | Stephens et al., 1987; |
| | Glue et al., 1988 |
| Hepatitis B Virus | Bulla et al., 1986; |
| | Jameel et al., 1986; |
| | Shaul et al., 1987; |
| | Spandau et al., 1988; |
| | Vannice et al., 1988 |
| Human Immunodeficiency Virus | Muesing et al., 1987; |
| | Hauber et al., 1988; |
| | Jakobovits et al., 1988; |
| | Feng et al., 1988; |
| | Takebe et al., 1988; |
| | Rosen et al., 1988; |
| | Berkhout et al., 1989; |
| | Laspia et al., 1989; |
| | Sharp et al., 1989; |
| | Braddock et al., 1989 |
| Cytomegalovirus (CMV) | Weber et al., 1984; |
| | Boshart et al., 1985; |
| | Foecking et al., 1986 |
| Gibbon Ape Leukemia Virus | Holbrook et al., 1987; |
| | Quinn et al., 1989 |

TABLE 2

Inducible Elements

| Element | Inducer | References |
|---|---|---|
| MT II | Phorbol Ester (TFA) | Palmiter et al., 1982; |
| | Heavy metals | Haslinger et al., 1985; |
| | | Searle et al., 1985; |
| | | Stuart et al., 1985; |
| | | Imagawa et al., 1987, |
| | | Karin et al., 1987; |
| | | Angel et al., 1987b; |
| | | McNeall et al., 1989 |
| MMTV (mouse mammary tumor virus) | Glucocorticoids | Huang et al., 1981; |
| | | Lee et al., 1981; |
| | | Majors et al., 1983; |
| | | Chandler et al., 1983; |
| | | Lee et al., 1984; |
| | | Ponta et al., 1985; |
| | | Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

In certain embodiments, the promoter may be a elongation factor 1a (EF1a), an inducible promoter such as tet$^R$, the one of the RU486 system or the meristerone system.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

B. Termination Signals

The LEEs and CEEs of the present invention will generally comprise at least one termination signal. A terminator is comprised of the DNA sequences involved in specific termination of an RNA transcript by an RNA polymerase. Thus, in certain embodiments a termination signal that ends the production of an RNA transcript is contemplated. However, in eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyAtail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the termination sequence and polyadenylation site of human growth hormone; termination sequences of house keeping genes including but not limited to actin or tubulin; or viral termination sequences. Including but not limited to eukayrotic viruses such as SV40, MMTV, Polyoma or HIV; or a lack of transcribable or translatable sequence, such as due to a sequence truncation.

C. Additional Components of Lees and Cees

The LEEs and CEEs may further comprise at least one additional regulatory sequence element involved with gene expression, or at least one additional sequence element to aid LEE or CEE construction or analysis. These additional elements may enhance or pause the expression and/or translation of the LEE or CEE sequences(s), enhance the immunogenicity of the gene-product, direct the gene product intracellularly, or aid in the preparation or analysis of the LEE or CEE. The additional sequence element may include, but is not limited to, at least one initiation signal, at least one internal ribosome binding site, at least one multiple cloning site, at least one splicing site, at least one marker, such as a selectable or screenable marker, or any combination thereof. The additional elements may be comprised in the 5' sequences and/or 3' sequences added to the ORF in the construction of the LEE or CEE.

1. Initiation Signals and Internal Ribosome Binding Sites

In certain embodiments, the LEE or CEE may comprise at least one initiation signal and/or at least one internal ribosome binding site. In specific aspects, a specific initiation signal may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

In certain embodiments, the LEE or CEE may comprise at least one multiple cloning site. A multiple cloning site (MCS) is a nucleic acid region that contains multiple restriction enzyme sites, any of which can be used in conjunction with standard recombinant technology to digest the constuct. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a construct is linearized or fragmented using a restriction enzyme that cuts within the MCS to enable exogenous sequences to be ligated to the construct. "Ligation" refers to the process of forming phosphodiester bonds between two nucleic acid fragments, which may or may not be contiguous with each other. Techniques involving restriction enzymes and ligation reactions are well known to those of skill in the art of recombinant technology. In certain aspects, the LEE or CEE may be digested to release various sequences, such as contained in the ORF, for size analysis or sequencing.

3. Splicing Sites

Most transcribed eukaryotic RNA molecules will undergo RNA splicing to remove introns from the primary transcripts. Constructs containing genomic eukaryotic sequences may require donor and/or acceptor splicing sites to ensure proper processing of the transcript for protein expression. (See Chandler et al., 1997, herein incorporated by reference.)

4. Selectable and Screenable Markers

In certain embodiments of the invention, the cells contain a LEE or CEE construct of the present invention, a cell may be identified in vitro or in vivo by including a marker in the LEE or CEE expression construct. Such markers would confer an identifiable change to the cell permitting easy identification of cells containing the expression construct. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP or LacZ, whose basis is colorimetric analysis; GUS whose basis is fluorescence; and LUC whose basis is lumenescence, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

5. Polyadenylation Signals

In eukaryotic expression, one may include at least one transcriptional terminator and at least one polyadenylation signal to effect termination and proper polyadenylation of the transcript. The nature of the terminator is not believed to be crucial to the successful practice of the invention, and any such sequence may be employed. Preferred embodiments include the SV40 terminator and/or the bovine growth hormone terminator, which are convenient and known to function well in various target cells. A terminator is comprised of at least one sequence signal of the end of transcription and may include a cleavage site that enables at least one polyadenylation siquence to be added. Polyadenylation may inclrease the stability of the transcript or may facilitate cytoplasmic transport. A terminator may be necessary in vivo to achieve desirable message levels.

D. Lee and Cee Vectors

In certain embodiments, the promoter and terminator sequences of the LEE or CEE may be regarded as a type of vector. The term "vector" is used to refer to a carrier nucleic acid molecule into which a nucleic acid sequence can be inserted for introduction into a cell where it can be expressed. A nucleic acid sequence can be "exogenous," which means that it is foreign to the cell into which the vector is being introduced or that the sequence is homologous to a sequence in the cell but in a position within the host cell nucleic acid in which the sequence is ordinarily not found.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In the case of LEEs and CEES, minimal control sequences comprising a promoter and/or a terminator may be added to the sequence that is to be expressed. In addition to a promoter and terminator, other control sequences that govern transcription and translation, vectors and expression vectors may contain nucleic acid sequences that serve other functions as well and are described infra.

E. Open Reading Frames (ORF)of Genes

The LEE or CEE may comprise at least one open reading frame (ORF). An open reading frame comprises a series of tri-nucleotides that encode one or more amino acids. An ORF is not interrupted by a termination codon (i.e., TAA, TAG, TGA). ORFs isolated from an organism may encode an endogenous peptide, polypeptide, protein or non-translated mRNA message. However, many ORFs do not encode for an endogeneously transcribed sequence.

In preferred aspects of the invention, ORFs are isolated from at least one organism, or a recombinant vector comprising nucleic acids from the organism. One or more organelles (i.e., mitochondria, chloroplasts), cells, tissues or organisms (including viruses) may be a source for the isolated promoters, open reading frames (i.e., genes), termination sequences and other sequences to be used in the construction of LEEs and CEEs. Methods of nucleic acid isolation are well known to one of ordinary skill in the art (see Sambrook et al. 1989). In other embodiments, the ORF can be synthetically built by known gene building techniques (Stemmer et al., 1995).

For screening a nucleic acid library, the screening or isolation protocol may utilize nucleotide segments or probes that are designed to hybridize to cDNA or genomic sequences of a desired ORF or surrounding sequence(s). Additionally, antibodies designed to bind to the ORF's expressed proteins, polypeptides, or peptides may be used as probes to screen an appropriate DNA expression library. Alternatively, activity assays may be employed. The operation of such screening protocols are well known to those of skill in the art and are described in detail in the scientific literature (Sambrook et al. 1989, incorporated herein by reference). Moreover, as the present invention encompasses the isolation and expression of genomic segments as well as cDNA molecules, it is contemplated that suitable genomic isolation methods, as known to those in the art, may also be used.

As used herein "designed to hybridize" means a sequence selected for its likely ability to hybridize to an ORF or surrounding sequence(s) due to the expected homology between the ORF or surrounding sequences and a related nucleic acid sequence probe or primer. Also included are segments or probes altered to enhance their ability to hybridize to or bind to an ORF or surrounding sequence(s). Additionally, these regions of homology also include amino acid sequences of 4 or more consecutive amino acids selected and/or altered to increase conservation of the amino acid sequences in comparison to the same or similar region of residues in the same or related genes in one or more species.

Such sequences may be used as probes for hybridization or oligonucleotide primers for PCR™. Designing such sequences may involve selection of regions of highly conserved nucleotide sequences between various species for a particular gene or related genes, relative to the general conservation of nucleotides of the gene or related genes in one or more species. Comparison of the amino acid sequences conserved between one or more species for a particular gene may also be used to determine a group of 4 or more consecutive amino acids that are conserved relative to the protein encoded by the gene or related genes. The nucleotide probe or primers may then be designed from the region of the gene that encodes the conserved sequence of amino acids.

However, random or semi-random probes and primers may be used to hybridize to or amplify ORFs and/or surrounding sequences. Such uncharacterized ORFs may be sequenced or screened for function using any technique described herein or known to one of ordinary skill in the art.

The nucleotide and protein, polypeptide and peptide sequences for various ORFs, promoters, termination sequences and genes have been previously disclosed, and may be found at computerized databases known to those of ordinary skill in the art. One such database is the National Center for Biotechnology Information's Genbank and Gen-Pept databases (http://www.ncbi.nlm.nih.gov/). The coding regions for these known genes may be amplified and/or expressed using the techniques disclosed herein or by any technique that would be know to those of ordinary skill in the art. Such nucleic or amino acid sequences may be used to screen for additional related ORFs, and may be used to construct LEEs or CEEs.

The isolated ORFs may then be operatively associated with a promoter, termination signal, and/or other sequence components to form a LEE or CEE. Expressed LEEs or CEEs may be assayed in vivo or in vitro for any activity or properties of the transcribed or translated sequences, using any applicable assay described herein or would be know to one of skill in the art.

F. Cells

In particular embodiments, promoters, ORFs, termination sequences other sequences may be isolated from at least one organelle, cell, tissue or organism. In other embodiments, at least one LEE or CEE may be transfected into at least one organelle, cell, tissue or organism. In particular aspects, the LEE or CEE's open reading frame is transcribed, and in more specific aspects, translated into a protein, polypeptide or peptide in the at least one organelle, cell, tissue or organism.

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon the desired purpose of the expression of the vector encoded ORF. Numerous cell lines and cultures are available for use as a host cell, and they can be obtained through the American Type Culture Collection (ATCC), which is an organization that serves as an archive for living cultures and genetic materials (www.atcc.org). In certain embodiments, a cell may comprise, but is not limited to, at least one skin, bone, neuron, axon, cartilage, blood vessel, cornea, muscle, facia, brain, prostate, breast, endometrium, lung, pancreas, small intestine, blood, liver, testes, ovaries, cervix, colon, skin, stomach, esophagus, spleen, lymph node, bone marrow, kidney, peripheral blood, embryonic or ascite cell, and all cancers thereof. An appropriate host can be determined by one of skill in the art based on the vector backbone and the desired result. Bacterial cells used as host cells for vector expression include DH5α, JM109BL21, and KC8, as well as a number of commercially available bacterial hosts such as SURE® Competent Cells and Solopack™ Gold Cells (Stratagene®La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, WelH and PC12. Many host cells from various cell types and organisms are available and would be known to one of skill in the art.

Some LEE or CEE vectors may employ control sequences that allow it to be expressed in both prokaryotic and eukaryotic cells. One of skill in the art would further understand the conditions under which to incubate all of the above described host cells to maintain them. Also understood and known are techniques and conditions that would allow large-scale production of vectors, as well as production of the nucleic acids encoded by vectors and their cognate polypeptides, proteins, or peptides.

1. Tissues

The cell or cells to be transformed with a LEE or CEE may be comprised in a tissue. The tissue may be part of or separated from an organism. In certain embodiments, a tissue may comprise, but is not limited to, skin, bone, neuron, axon, cartilage, blood vessel, cornea, muscle, facia, brain, prostate, breast, endometrium, lung, pancreas, small intestine, blood, liver, testes, ovaries, cervix, colon, skin, stomach, esophagus, spleen, lymph node, bone marrow, kidney, peripheral blood, embryonic, ascite tissue, meristematic cells, pollen, leaves, anthers, roots, root tips, silk, flowers, kernels, ears, cobs, husks, stalks, and all cancers thereof.

2. Organisms

In certain embodiments, the cell or tissue may be comprised in at least one organism. In certain embodiments, the organism may be, but is not limited to, an eubacteria, an archaea, an eukaryote or a virus (see webpage http://phylogeny.arizona.edu/tree/phylogeny.html).

a. Eubacteria

In certain embodiments, the organism is an eubacteria. In particular embodiments, the eubacteria may be, but is not limited to, an aquifecales; a thermotogales; a thermodesulfobacterium; a member of the thermus-deinococcus group; a chloroflecales; a cyanobacteria; a firmicutes; a member of the leptospirillum group; a synergistes; a member of the chlorobium-flavobacteria group; a member of the chlamydia-verrucomicrobia group, including but not limited to a verrucomicrobia or a chlamydia; a planctomycetales; a flexistipes; a member of the fibrobacter group; a spirochetes; a proteobacteria, including but not limited to an alpha proteobacteria, a beta proteobacteria, a delta & epsilon proteobacteria or a gamma proteobacteria. In certain aspects, an organelle derived from eubacteria are contemplated, including a mitochondria or a chloroplast.

b. Archaea

In certain embodiments, the organism is an archaea (a.k.a. archaebacteria; e.g., a methanogens, a halophiles, a sulfolobus). In particular embodiments, the archaea may be, but is not limited to, a korarchaeota; a crenarchaeota, including but not limited to, a thermofilum, a pyrobaculum, a thermoproteus, a sulfolobus, a metallosphaera, an acidianus, a thermodiscus, a igneococcus, a thermosphaera, a desulfurococcus, a staphylothermus, a pyrolobus, a hyperthermus or a pyrodictium; or an euryarchaeota, including but not limited to a halobacterilaes, methanomicrobilaes, a methanobacteriales, a methanococcales, a methanopyrales, an archeoglobales, a thermoplasmales or a thermococcales.

c. Eukaryotes

In certain embodiments, the organism is an eukaryote (e.g., a protist, a plant, a fungi, an animal). In particular embodiments, the eukaryote may be, but is not limited to, a microsporidia, a diplomonad, an oxymonad, a retortamonad, a parabasalid, a pelobiont, an entamoebae or a mitochondrial eukaryote (e.g., an animal., a plant, a fungi, a stramenopiles).

In certain embodiments, the mitochondrial eukaryote may be, but is not limited to, a metazoa (e.g., an animal), a myxozoa, a choanoflagellate, a fungi (e.g., a mushroom, a mold, a yeast, a chytrid), a green plant (e.g., a green algae, a land plant), a cryptomonad, an ancyromona, plasmodiophorid, a rhodophyta, a centrohelid heliozoa, a cyanophorid, an alveolate (e.g., a dinoflagellate, a sporozoan, a ciliate), a stramenopile (e.g., a brown algae, a diatoms, an oomycete, a chrysophyte), an acantharea, a vampyrellid, a thaumatomonad, a telonema, a sticholonche, a spongomonad, a ramicristate, a pseudospora, a pseudodendromonad, a phalansterium, a phaeodarean radiolaria, a paramyxea, a luffisphaera, a leucodictyon, a kathablepharid, a histiona, a haptophyte, an ebriid, a discocelis, a diphylleia, a eesmothoracid, a cryothecomona, a copromyxid, a chlorarachnion, a cercomonad, a caecitellus, an apusomonad, an actinophryid or an acanthamoebae.

In particular aspects, the eukaryote is a metazoa (e.g., an animal). In certain aspects, the metazoa may be, but is not limited to, a porifera (e.g., a sponge), a cnidaria (e.g., a jellyfish, an anemone, a coral.), a ctenophora (e.g., a combjelly), an arthropoda (e.g., an insect, a spider, a crab), an annelida (e.g., a segmented worm), a pogonophora, a vestimentifera, an echiura, a mollusca (e.g., a snail, a clam, a squid), a sipuncula, a nemertea (e.g., a ribbon worm), a platyhelminthes (e.g., a flatworm), a chordata (e.g., a vertebrate), a hemichordata, a lophophorates, a chaetognatha, an echinodermata (e.g., a starfish, a urchin, a sea cucumber), a pseudocoelomates, a placozoa, a monoblastozoa, rhomobozoa, an orthonectida. In particular facets the vertebrate may be a terrestrial vertebrate (e.g., a frog, a salamander, a caecilian, a reptile, a mammal, a bird) or a non-terrestrial vertebrate (e.g., a sharks, a ray, a sawfish, a chimera, a ray-finned fish, a lobe-finned fish). In additional facets, the mammal may be a monotremata (e.g., a platypus, an echidna), a multituberculata, a marsupialia (e.g., an opossum, a kangaroo), a palaeoryetoids or an eutheria (e.g., a placental mammal).

In particular facets the eutheria may be, but is not limited to, an edentata (e.g., an anteater, a sloth, an armadillo), a pholidota (e.g., a pangolin), a lagomorpha (e.g., a rabbits), a glires, a rodentia (e.g., a mouse, a rat, a squirrel, a gopher, a porcupine, a beaver), a macroscelidea (e.g., an elephant shrew), a primates (e.g., a monkey, a lemur, a gorilla, a chimp, a human), a scandentia (e.g., a tree shrew), a chiroptera (e.g., a bat), a dermoptera (e.g., a colugo, a flying lemur), an insectivora (e.g., a shrew, a mole, a hedgehog), a creodonta, a carnivora (e.g., a dog, a cat, a bear, a raccon, a weasel, a mongoose, a hyena), a condylarthra, an artiodactyla (e.g., a pig, a deer, a cattle, a goat, a sheep, a hippopotamus, a camel), a cetacea (e.g., a whale, a dolphin, a porpoise), a tubulidentata (e.g., an aardvark), a perissodactyla (e.g., a horse, a tapir, a rhinoceros), a hyracoidea (e.g., a hyrax, a dassy), a sirenia (e.g., a manatee, a dugong, a sea cow), a desmostylia, an embrythopoda, or a proboscidea (e.g., an elephant).

In particular embodiments, eukaryote is a fungi. A fungi may be, but is not limited to, a chytridiomycota (e.g., a water mold, an allomyces), a zygomycota (e.g., a bread mold, a rhizopus, a mucor), a basidiomycota (e.g., a mushroom, a rust, a smut) or an ascomycota (e.g., a sac fungi, a yeast, a penicillium).

In certain embodiments, the eukaryote is a green plant. A green plant may be, but is not limited to, a prasinophytes, a chlorophyceae, a trebouxiophyceae, a ulvophyceae, a chlorokybales, a klebsormidiales, a zygnematales, a streptophyta, a charales, a coleochaetales or an embryophytes (e.g., a land plant). In particular facets, the embryophytes may be, but is not limited to, a marchantiomorpha (e.g., a liverwort), an Anthoceromorpha (e.g., a hornwort), a bryopsida (e.g., a moss), a lycopsida (e.g., a lycophyte), an equisetopsida (e.g., a horsetail, a sphenophyte), a filicopsida (e.g., a fern), a spermatopsida (e.g., a seed plant: a flowering plant, a conifer). In particular aspects, the spermatopsida may be, but is not limited to an angiosperm. An angiosperm may include, but is not limited to, a ceratophyllaceae, a nymphaeales, a piperales, an aristolochilaes, a monocotyledons, an eudicots, a laurales, a chloranthaceae, a winterales or a magnoliales.

d. Viruses

In certain embodiments the organism may be a virus. In particular aspects, the virus may be, but is not limited to, a DNA Virus, including but not limited to a ssDNA virus or a dsDNA virus; a DNA RNA rev transcribing virus; a RNA virus, including but not limited to a dsRNA virus, including but not limited to a −ve stranded ssRNA or a +ve stranded ssRNA; or an unassigned virus.

G. Production of Lees and Cees

The invention further relates to methods of producing a LEE or CEE. Methods for producing a LEE or CEE will generally comprise obtaining a DNA segment comprising an ORF and linking the ORF to a promoter, terminator, or other molecule to create a LEE or CEE.

The ORF, promoter, terminator or additional nucleic acid(s) may be obtained by any method described herein or as would be known to one of ordinary skill in the art, including nucleic acid amplification or chemical synthesis of nucleic acids. Non-limiting examples of synthetic nucleic acid, particularly a synthetic oligonucleotide, include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. Ser. No. 5,705,629, each incorporated herein by reference. A non-limiting example of enzymatically produced nucleic acid include one produced by enzymes in amplification reactions such as PCR™ (see for example, U.S. Pat. Nos. 4,683,202 and 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

In certain aspect, the present invention concerns at least one promoter, terminator, ORF and/or other nucleic acid that is an isolated nucleic acid. As used herein, the term "isolated nucleic acid" refers to at least one nucleic acid molecule that has been isolated free of, or is otherwise free of, the bulk of the total genomic and transcribed nucleic acids of one or more organelles, cells, tissues or organisms. In certain embodiments, "isolated nucleic acid" refers to a nucleic acid that has been isolated free of, or is otherwise free of, bulk of cellular components and macromolecules such as lipids, proteins, small biological molecules, and the like. As different species may have a RNA or a DNA containing genome, the term "isolated nucleic acid" encompasses both the terms "isolated DNA" and "isolated RNA". Thus, the isolated nucleic acid may comprise a RNA or DNA molecule isolated from, or otherwise free of, the bulk of total RNA, DNA or other nucleic acids of a particular species. As used herein, an isolated nucleic acid isolated from a particular species is referred to as a "species specific nucleic acid." When designating a nucleic acid isolated from a particular species, such as human, such a type of nucleic acid may be identified by the name of the species. In a non-limiting example, a nucleic acid isolated from one or more humans would be an "isolated human nucleic acid."

The linking of an ORF to a promoter, terminator and/or an additional molecule (i.e., another nucleic acid), may be a covalent or non-covalent attachment or association. In a non-limiting example, a non-covalent association contemplated may be simply admixing a promoter, terminator and/or additional nucleic acid with the ORF nucleic acid. In a more preferred embodiment, one or more of ends of the promoter, terminator, additional molecule and/or ORF comprise complementary nucleic acids that promote annealing of one or more ends of the promoter, terminator, additional molecule and/or ORF to themselves or to each other. If one or more of the nucleic acids are double stranded, the end that is complementary may be an overhanging single strand from the double stranded molecule. Single-stranded regions of sufficient length and/or complementary anneal, and the attached components may be directly delivered into a cell, tissue or organism.

In one method that may be employed, a dUMP-containing tail is synthesized at the 5' end of PCR® primers. Following amplification, uracil DNA glycosylase (UDG) is used to cleave the glycosylic bond between the sugar and base. This creates an abasic site which destabilizes base-pairing in the double-stranded DNA and creates a 5' single-stranded overhang available for linking.

LEEs and CEEs may be made by any number of methods other than the dU method described above. For example, there are multiple examples in the literature of methods of generating overhangs for plasmid cloning. The inventors have used the below-described alternative methods for generating the overhangs typically employed in producing LEEs.

For example, abasic phosphoramidates may be used. PCR® primers are synthesized so as to contain a "base-less" phosphoramidite at a position where one desires the single-stranded/double-stranded junction to be on the final PCR® product. This "nucleotide" has no sugar residue, therefore during amplification Taq polymerase stops when it reaches this position, leaving a protruding 5' end. In one drawback of this method, the modified phosphoramidite is unstable and as a result the whole primer that is made for this purpose is unstable. A related method involves the use of dSpacer phosphoramidates. These are used in the same way as abasics: PCR® primers are built that contain a modified phosphoramidite at some position where one desires the single-stranded/double-stranded junction to be on the final PCR® product. In this case, the stability of the abasic site was improved by inserting a "base-like" structure in position of the base. The synthetic abasic and dSpacer methods tend to be inefficient, in that they require the synthetic oligo regions of the PCR® product (the 5' overhangs) to anneal.

Methods involving T4 DNA polymerase may be used to create overhangs. The exonuclease activity of this enzyme is used to digest the 3' ends of PCR® products, resulting in a 5' single-stranded overhang. The extent of the digestion (and therefore the length of the overhang) is controlled by designing a primer with a specific sequence that lacks one of the four nucleotide bases from the 5' end until the desired double/single-stranded junction point. Only the nucleotide to pair with this position is provided during digestion.

One can use rU/RNase A to create LEEs. This method is conceptually similar to the dU/UDG method. However, instead of a DNA (dU) version of uracil, one can use the RNA molecule (rU) to incorporate into PCR® primers. These primers were used for standard PCR® amplification. To generate the overhangs one simply exposes the PCR® product to RNaseA, which is far cheaper than UDG. This method works well but has a drawback in the instability of RNA-containing primers relative to completely DNA primers.

Methods involving long/short PCR® priming are useful to prepare LEEs. One can design two primers for one side of a PCR® product, with one sitting down on the template 12–15 nucleotides upstream of the other. Amplification with both primers in addition to the usual one at the other end generated three types of annealed products: 2 longs (25%), 2 shorts (25%), and 1 long/1 short (50% of the population). The long/short products are the useful products with single-stranded overhangs.

With appropriate modifications, each of these technologies can be employed to make CEEs as well as LEEs.

To enable annealing of single stranded ends, the ends are preferably complementary or semi-complementary. Designing complementary or semi-complementary sequences of nucleic acids are well know to one of ordinary skill in the art. Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, that are capable of hybridizing or annealing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during hybridization or annealing. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization or annealing.

In certain embodiments, the complementary or semi-complementary ends of the ORF, promoter, terminator and/or additional molecule promote non-covalent association of their ends, in any combination desired or designed by a skilled practitioner. Thus, linear or circular conformations of the ORF, promoter, terminator and/or additional. molecule are contemplated through non-covalent associations. In other aspects, the semi-complementary or complementary ends may promote enzymatic ligation. Of course, one or more ends of an ORF, promoter, terminator and/or additional molecule may be designed to promote annealing to form linear or circular elements. Alternatively, the promoter, terminator, ORF and/or additional molecule may be synthetically or biologically produced as one nucleic acid.

In a preferred embodiment, one or more ORFs would be amplified, and then be linked (i.e., associated, annealed, and/or ligated) to a standard promoter and/or terminator. For example, most gene screening assays will require fusing a common promoter and/or terminator to a variety of ORFs, or a reporter ORF to a variety of promoters and/or terminators. In a non-limiting example, screening genes in mammalian cells would require fusing the ORFs to a eukaryotic promoter and terminator. Therefore, an ideal LEE system will typically involve amplification of only an ORF which would then be linked to a set of standard promoter and/or terminator sequences. In certain embodiments, the promoter, terminator and/or ORF are produced via amplification as one unit.

In additional embodiments, it is not required for all applications that a terminator be provided. For instance, in methods involving cell-free expression, no terminator may be required.

Though not required, a nucleic acid, such as a promoter, ORF, terminator, LEE or CEE may be purified on polyacrylamide gels, cesium chloride centrifugation gradients, filter gradient or by any other means known to one of ordinary skill in the art (see for example, Sambrook et al. 1989, incorporated herein by reference).

H. Methods of Lee and Cee Delivery

Suitable methods for LEE or CEE delivery for transformation or a organelle, cell, tissue or organim for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S.

Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, organelle(s), cell(s), tissue(s) or organism(s) may be stably or transciently transformed. In certain embodiments, acceleration methods are preferred and include, for example, microprojectile bombardment and the like.

1. Injection

In certain embodiments, the LEE or CEE may be delivered via one or more injections, for example, either subcutaneously, intradermally or intramuscularly.

Figure 7A:
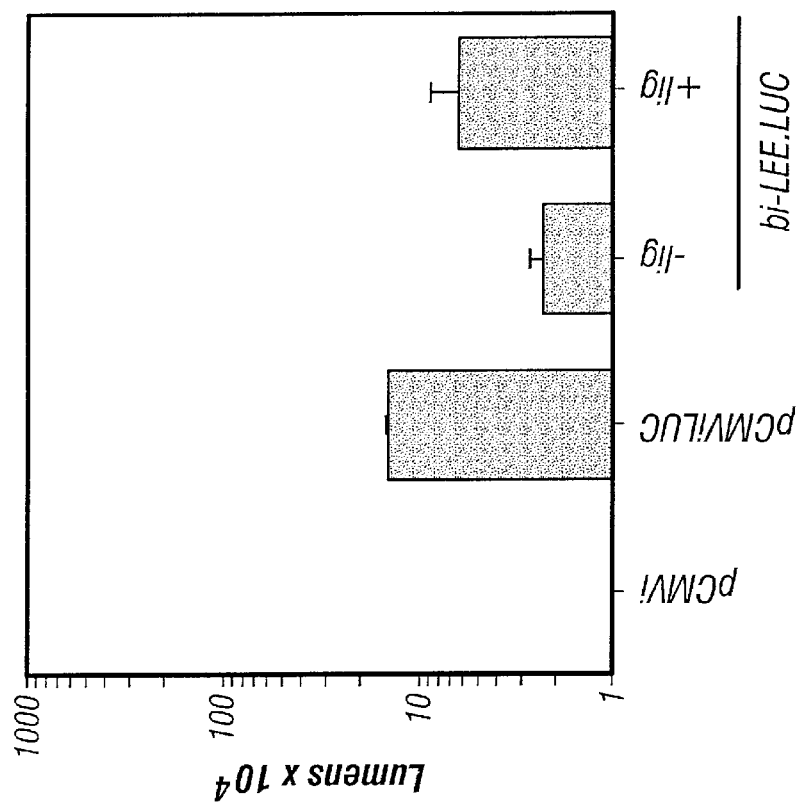
FIG. 7A, FIG. 7B, and FIG. 7C. LEEs can be delivered into animals biolistically, by needle injection and by lipid-mediated uptake.
Figure 7B:
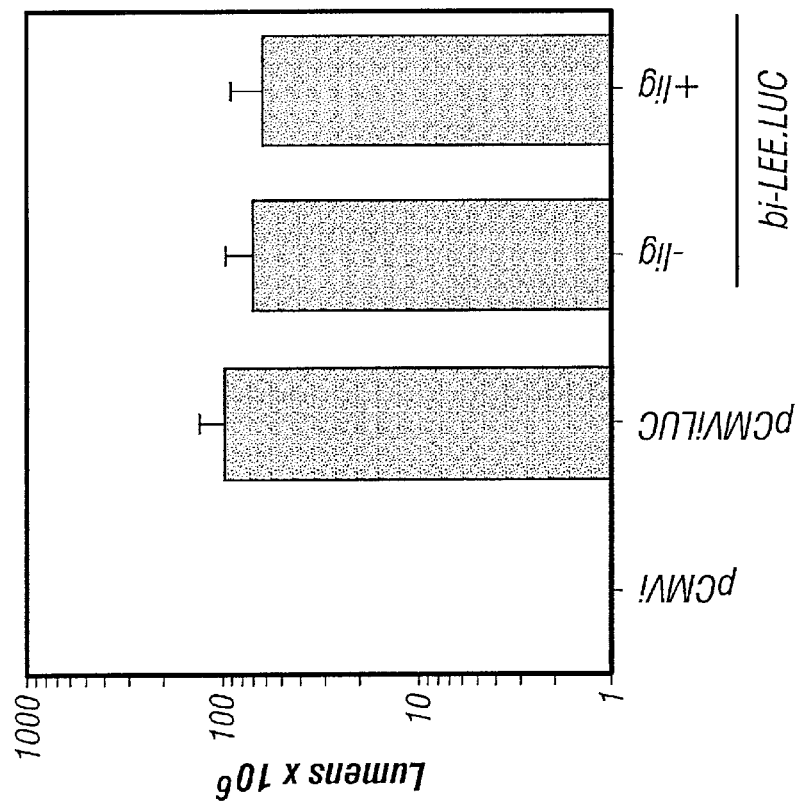
Figure 7C:
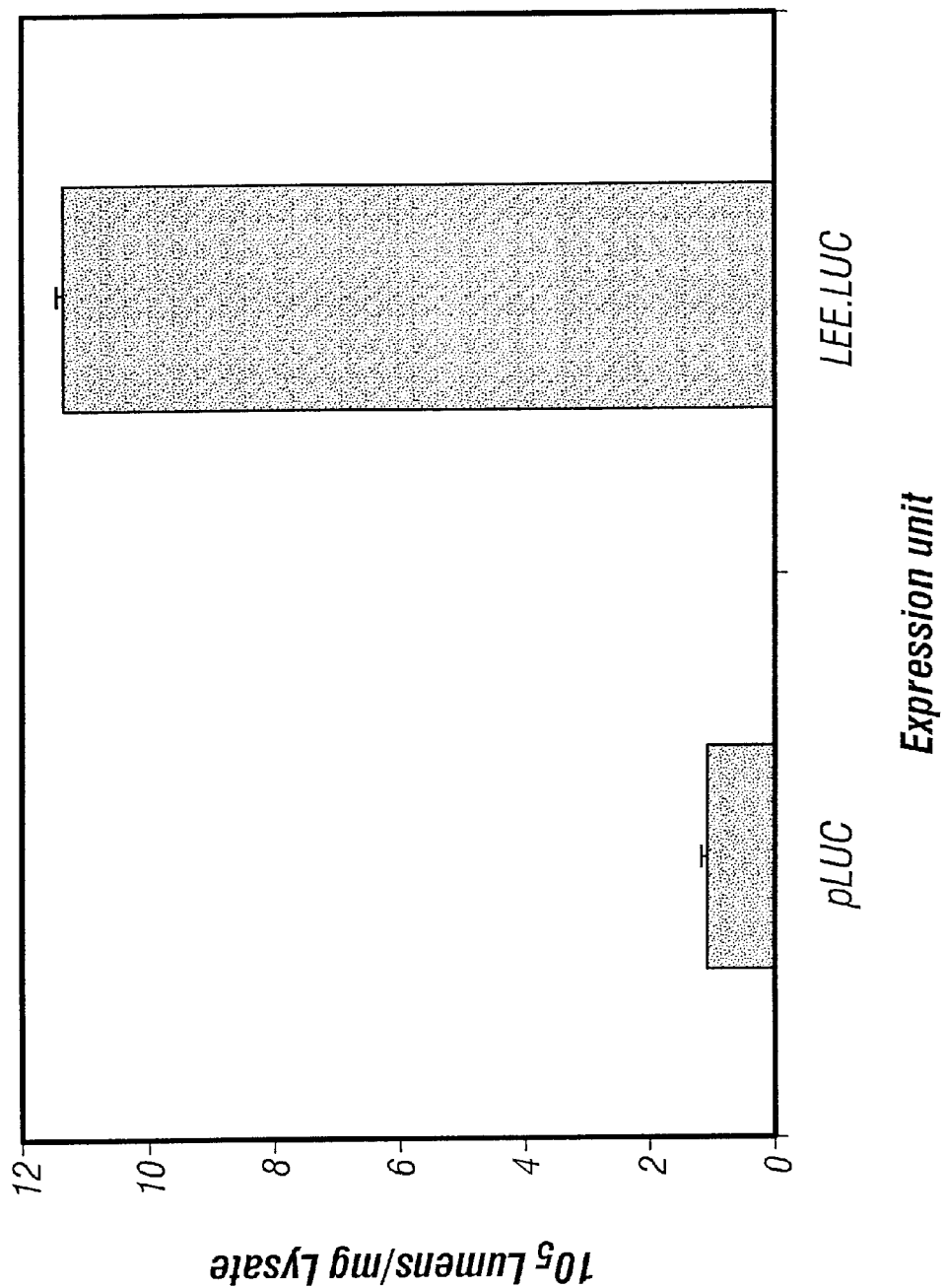

The data in FIG. 7A and FIG. 7B show that PCR®-generated LEEs can be used with other transfection protocols such as an injection (i.e., a needle injection). When the supercoiled, replicative control plasmid and LEE vectors were introduced intramuscularly (i.m.) by needle injection in a saline solution, the LUC activity encoded by the noncovalently linked LEE was 15% of that produced by the LUC plasmid. Addition of ligase to the LEE prior to injection raised LUC activity to 41% of the plasmid standard (FIG. 7B). By contrast, addition of ligase did not further improve expression from LEEs introduced with the gene gun, which was similar to the plasmid standard (FIG. 7A). These results are consistent with the observation that the gene-gun delivers samples directly inside skin cells (Williams et al., 1991) while a needle introduces DNA into the extracellular space of muscle tissue (Wolff et al., 1990), where exonucleases are prevalent.

2. Electroporation

In certain embodiments of the present invention, the LEE or CEE is introduced into the cell via electroporation. Electroporation involves the exposure of a suspension of cells and DNA to a high-voltage electric discharge. Where one wishes to introduce DNA by means of electroporation, it is contemplated that the method of Krzyzek et al. (U.S. Pat. No. 5,384,253, incorporated herein by reference in its entirety) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, but not limited to, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

3. Microprojectile Bombardment

Microprojectile bombardment techniques are a preferred method of introducing CEEs and LEEs into at least one, organelle, cell, tissue or organism (U.S. Pat. Nos. 5,550,318; 5,538,880; 5,610,042; and PCT Application WO 94/09699; each of which is specifically incorporated herein by reference in its entirety). There are a wide variety of microprojectile bombardment techniques known in the art, many of which are applicable to the invention. However, the inventors have used the general protocol described in the specific examples. In some of the studies described herein the specific examples, genes were introduced into skin cells with a gene gun (Examples 2, 3, 4, 9, 10, 11 and 16).

In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into cells, including but not limited to plant cells, by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually various cells, tissues or organism, such as for example any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general. (U.S. Pat. No. 5,563,055, specifically incorporated herein by reference in its entirety).

4. Liposome-Mediated Transfection

In a further embodiment of the invention, a LEE or CEE may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an expression construct complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome.

5. Calcium Phosphate or DEAE-Dextran

In other embodiments of the present invention, the LEE or CEE is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the LEE or CEE is delivered into the cell using DEAE-dextran followed by polyethylene glycol. In this manner, reporter plasmids were introduced into mouse myeloma and erythroleukemia cells (Gopal., 1985).

6. Direct Microinjection or Sonication Loading

Further embodiments of the present invention include the introduction of the LEE or CEE by direct microinjection or sonication loading. Direct microinjection has been used to introduce nucleic acid constructs into Xenopus oocytes (Harland and Weintraub, 1985), and LTK⁻ fibroblasts have been transfected with the thymidine kinase gene by sonication loading (Fechheimer et al., 1987).

7. Receptor Mediated Transfection

Still further, LEEs or CEEs that may be employed to deliver nucleic acid constructs to target cells are receptor-mediated delivery vehicles. These take advantage of the selective uptake of macromolecules by receptor-mediated endocytosis that will be occurring in the target cells. In view of the cell type-specific distribution of various receptors, this delivery method adds another degree of specificity to the present invention. Specific delivery in the context of another mammalian cell type is described by Wu and Wu (1993; incorporated herein by reference).

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. In certain aspects of the present invention, the ligand will be chosen to correspond to a receptor specifically expressed on the EOE target cell population.

In other embodiments, the DNA delivery vehicle component of a cell-specific gene targeting vehicle may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding. For example, Nicolau et al. (1987) employed lactosyl-ceramide, a galactose-terminal asialganglioside, incorporated into liposomes and observed an increase in the uptake of the insulin gene by hepatocytes. It is contemplated that the tissue-specific transforming constructs of the present invention can be specifically delivered into the target cells in a similar manner.

8. Plant Directed Transformation Techniques a. Agrobacterium-mediated Transformation Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; Zhang et al., 1997; U.S. Pat. No. 5,591,616, specifically incorporated herein by reference in its entirety), wheat (McCormac et al., 1998), barley (Tingay et al., 1997; McCormac et al., 1998), and maize (Ishidia et al., 1996).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

b. Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Fujimara et al., 1985; Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cell are punctured. This technique has been used successfully with, for example, the monocot cereals maize (PCT Application WO 95/06128, specifically incorporated herein by reference in its entirety; Thompson, 1995) and rice (Nagatani, 1997).

I. Non-protein-expressing Sequences

In certain embodiments, the LEE or CEE may express messages that are not translated. DNA may be introduced into organisms for the purpose of expressing RNA transcripts that function to affect phenotype yet are not translated into protein. Two examples are antisense RNA and RNA with ribozyme activity. Both may serve possible functions in reducing or eliminating expression of native or introduced genes. However, as detailed below, DNA need not be expressed to effect the phenotype of an organism.

1. Antisense RNA

In certain aspects, a LEE or CEE may express an antisense message. ORFs, particularly those from genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the cell's genome. The aforementioned genes will be referred to as antisense genes. An antisense gene may thus be introduced into a cell by transformation methods to produce a novel transgenic cell or organism with reduced expression of a selected protein of interest. For example, the protein may be an enzyme that catalyzes a reaction in the cell or organism. Reduction of the enzyme activity may reduce or eliminate products of the reaction which include any enzymatically synthesized compound in the cell or organism such as fatty acids, amino acids, carbohydrates, nucleic acids and the like.

Alternatively, in a non-limiting example such as the transformation of a plant cell, the protein may be a storage protein, such as a zein, or a structural protein, the decreased expression of which may lead to changes in seed amino acid composition or plant morphological changes respectively. The possibilities cited above are provided only by way of example and do not represent the full range of applications.

2. Ribozymes

In other aspects, the LEE or CEE may produce a ribozyme. ORFs may be constructed or isolated which, when transcribed, produce RNA enzymes (ribozymes) that can act as endoribonucleases and catalyze the cleavage of RNA molecules with selected sequences. The cleavage of selected messenger RNAs can result in the reduced production of their encoded polypeptide products. These genes may be used to prepare novel one or more cells, tissues and organisms which possess them. The transgenic cells, tissues or organisms may possess reduced levels of polypeptides including, but not limited to, the polypeptides cited above.

Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes.

Several different ribozyme motifs have been described with RNA cleavage activity (Symons, 1992). Examples include sequences from the Group I self splicing introns including Tobacco Ringspot Virus (Prody et al., 1986), Avocado Sunblotch Viroid (Palukaitis et al., 1979), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994, U.S. Pat. Nos. 5,168,053 and 5,624,824), hairpin ribozyme structures (Berzal-Herranz et al., 1992; Chowrira et al., 1993) and Hepatitis Delta virus based ribozymes (U.S. Pat. No. 5,625,047). The general design and optimization of ribozyme directed RNA cleavage activity has been discussed in detail (Haseloff and Gerlach, 1988, Symons, 1992, Chowrira et al., 1994; Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Perriman et al., 1992; Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in down regulating a given gene is simply a matter of preparing and testing a given sequence, and is a routinely practiced "screening" method known to those of skill in the art.

3. Induction of Gene Silencing

In additional aspects, the LEE or CEE may be transcribed to promote gene silencing. It also is possible that ORFs derived from genes may be introduced to produce novel cells, tissues and organisms which have reduced expression of a native gene product by the mechanism of co-suppression. It has been demonstrated in tobacco, tomato, and petunia (Goring et al., 1991; Smith et al., 1990; Napoli et al., 1990; van der Krol et al., 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

4. Non-RNA-Expressing Sequences

In further embodiments, LEE or CEEs may be used to tag a cell, tissue or organism, or mutate a gene. DNA elements including those of transposable elements such as Ds, Ac, or Mu, may be inserted into a gene to cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired, may be isolated, cloned and manipulated as desired. The utility of DNA elements introduced into an organism for purposes of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences, could be introduced into cells, tissues and organims as proprietary "labels" of those cells, tissues and organisms, particularly plants and seeds thereof. It would not be necessary for a label DNA element to disrupt the function of a gene endogenous to the host organism, as the sole function of this DNA would be to identify the origin of the cell, tissue or organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief, 1989), which can be positioned around an expressible gene of interest to effect an increase in overall expression of the gene and diminish position dependent effects upon incorporation into the genome, particularly a plant genome (Stief et al., 1989; Phi-Van et al., 1990).

J. Exogenous Genes for Modification of Plant Phenotypes

A particularly important advance of the present invention is that it provides methods and compositions for the efficient expression of selected proteins in plant cells. LEE and CEE constructs may be made with various plant specific promoters. Promoters for plant specific expression are known to those of skill in the art, and include but are not limited to, any constitutive, inducible, tissue or organ specific, or developmental stage specific promoter which can be expressed in the particular plant cell. Suitable such promoters are disclosed in Weising et al., supra.

Promoters suitable for use herein include, but are not limited to, at least one regulatory sequence from the T-DNA of A. tumefaciens, including mannopine synthase, nopaline synthase, and octopine synthase; alcohol dehydrogenase promoter from corn; light inducible promoters such as ribulose-biphosphate-carboxylase small subunit gene from a variety of species and the major chlorophyll a/b binding protein gene promoter; histone promoters (EP 507 698), actin promoters; maize ubiquitin 1 promoter (Christensen et al. (1996) Transgenic Res. 5:213); 35S and 19S promoters of cauliflower mosaic virus; developmentally regulated promoters such as the waxy, zein, or bronze promoters from maize; as well as synthetic or other natural promoters which are either inducible or constitutive, including those promoters exhibiting organ specific expression or expression at specific development stage(s) of the plant, like the alpha-tubulin promoter disclosed in U.S. Pat. No. 5,635,618.

Other elements such as introns, enhancers, termination sequences and the like, may also be present in the LEE or CEE. These elements must be compatible with the remainder of the LEE or CEE gene constructions. Such elements may or may not be necessary for the function of the gene, although they may provide a better expression or functioning of the gene by effecting transcription, stability of the mRNA, or the like. Such elements may be included in the nucleic acid as desired to obtain the optimal. performance of the transforming gene in the organism, such as but not limited to a plant. In a non-limiting example, the maize Adh1S first intron maybe placed between the promoter and the coding sequence of a particular heterologous nucleic acid. This intron, when included in a gene construction, is known to generally increase expression in maize cells of a protein. (Callis et al. (1987) Genes Dev. 1:1183). Other suitable introns include, but are not limited to, at least one first intron of the shrunken-1 gene of maize (Maas et al. (1991) Plant Mol. Biol. 16:199); the first intron of the castor bean catalase (cat-1) gene (Ohta et al. (1990) Plant Cell Physiol. 31:805); potato catalase second intron of the ST-LSI gene (Vancanneyt et al. (1990) Mol. Gen. Genet. 220:245); tobacco yellow dwarf virus DSV intron (Morris et al. (1992) Virology 187:633; actin-1 (act-1) intron from rice (McElroy et al. (1990) Plant Cell 2:163); and triose phosphate isomerase (TPI) intron 1 (Snowden et al. (1996) Plant Mol. Biol. 31:689). However, sufficient expression for a gene to perform satisfactorily can often by obtained without an intron. (Battraw et al. (1990) Plant Mol. Biol. 15:527).

The LEE or CEE construct comprising the heterologous nucleic acid may also comprise sequences coding for a transit peptide, to drive the protein coded by the heterologous gene into an organelle (e.g., a chloroplast) of the plant cells. Such transit peptides are well known to those of ordinary skill in the art, and may include single transit peptides, as well as multiple transit peptides obtained by the combination of sequences coding for at least two transit peptides. One transit peptide is the Optimized Transit Peptide disclosed in U.S. Pat. No. 5,635,618, comprising in the direction of transcription a first DNA sequence encoding a first chloroplast transit peptide, a second DNA sequence encoding an N-terminal domain of a mature protein naturally driven into the chloroplasts, and a third DNA sequence encoding a second chloroplast transit peptide.

The choice of a selected protein for expression in a plant host cell in accordance with the invention will depend on the purpose of the transformation. One of the major purposes of transformation of crop plants is to add commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress and oxidative stress; increased yields; food content and makeup; physical appearance; male sterility; drydown; standability; prolificacy; starch quantity and quality; oil quantity and quality; protein quality and quantity; amino acid composition; and the like. Various U.S. Patents describe ORFs that may be used to confer these traits, such as U.S. Pat. Nos. 5,550,318, 6,023,013 and 6,040,497, each incorporated herein by reference.

In certain embodiments of the invention, transformation of a recipient cell may be carried out with more than one exogenous (selected) gene (i.e., ORF). As used herein, an "exogenous coding region" or "selected coding region" is a coding region not normally found in the host genome in an identical context. By this, it is meant that the coding region may be isolated from a different species than that of the host genome, or alternatively, isolated from the host genome, but is operably linked to one or more regulatory regions which differ from those found in the unaltered, native gene. Two or more exogenous coding regions also can be supplied in a single transformation event using either distinct transgene-encoding LEE or CEE constructs, or using a single construct incorporating two or more coding sequences.

K. Gene Vaccines

In certain embodiments, the at least one LEE or CEE comprise or express an antigen. The antigen may promote an immune response by an animal transfected or inoculated with the LEE or CEE encoding an antigen, or the LEE or CEE encoded antigen. Thus, the LEE or CEE may comprise a vaccine or "gene vaccine" useful for immunization protocols. In this embodiment, ORFs encoding antigens for pathogenic (e.g., HIV, SIV, mycoplasma), parasitic or allergenic organisms are preferred. Additionally, ORFs for putative antigens or allergens may be assayed for immunoreactions in one or more eukaryotic organisms.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the pathogen can be performed, following immunization.

1. Immunomodulators

It is contemplated that immunomodulators can be included in the vaccine to augment the patient's response. Immunomodulators can be included as purified proteins or their expression engineered into the cells when cells are part of the composition. Genes encoding immunomodulators can be included. The following sections list examples of immunomodulators that are of interest.

a. Cytokines

Interleukins and cytokines, and vectors expressing interleukins and cytokines are contemplated as possible vaccine components. Interleukins and cytokines, include but not limited to interleukin 1, IL-2, IL-3, IL-4, IL-5, IL-6, IL-7, IL-8, IL-9, IL-10, IL-11, IL-12, IL-13, IL-14, IL-15, β-interferon, α-interferon, γ-interferon, angiostatin, thrombospondin, endostatin, METH-1, METH-2, GM-CSF, G-CSF, M-CSF, tumor necrosis factor, and combinations thereof.

a. Cofactors

Cofactors or genes that encode cofactors may be used in the vaccine. Examples of cofactors include, but are not limited to CD85, CD80, B7.1, B7.2, etc.

b. Chemokines

Chemokines or ORFs that code for chemokines also may be used as vaccine components. Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Such chemokines include RANTES, MCAF, MIP1-alpha, MIP1-Beta, and IP-10. The skilled artisan will recognize that certain cytokines are also known to have chemoattractant effects and could also be classified under the term chemokines.

2. Adjuvants

Immunization protocols have used adjuvants to stimulate responses for many years. Some adjuvants affect the way in which antigens are presented. For example, the immune response is increased when protein antigens are precipitated by alum. Emulsification of antigens also prolongs the duration of antigen presentation. Other adjuvants, for example, certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

Adjuvants have been used experimentally to promote a generalized increase in immunity against unknown antigens (e.g., U.S. Pat. No. 4,877,611). This has been attempted particularly in the treatment of cancer. For many cancers, there is compelling evidence that the immune system participates in host defense against the tumor cells, but only a fraction of the likely total number of tumor-specific antigens are believed to have been identified to date. However, using the present invention, the inclusion of a suitable adjuvant into the membrane of an irradiated tumor cell will likely increase the anti-tumor response irrespective of the molecular identification of the prominent antigens. This is a particularly important and time-saving feature of the invention.

Those of skill in the art will know the different kinds of adjuvants that can be conjugated to cellular vaccines in accordance with this invention and these include alkyl lysophosphilipids (ALP); BCG; and biotin (including biotinylated derivatives) among others. Certain adjuvants particularly contemplated for use are the teichoic acids from Gram –ve cells. These include the lipoteichoic acids (LTA), ribitol teichoic acids (RTA) and glycerol teichoic acid (GTA). Active forms of their synthetic counterparts may also be employed in connection with the invention (Takada et al., 1995a).

Hemocyanins and hemoerythrins may also be used in the invention. The use of hemocyanin from keyhole limpet (KLH) is particularly preferred, although other molluscan and arthropod hemocyanins and hemoerythrins may be employed.

Various polysaccharide adjuvants may also be used. For example, Yin et al., (1989) describe the use of various pneumococcal polysaccharide adjuvants on the antibody responses of mice. The doses that produce optimal responses, or that otherwise do not produce suppression, as indicated in Yin et al., (1989) should be employed. Polyamine varieties of polysaccharides are particularly preferred, such as chitin and chitosan, including deacetylated chitin.

A further preferred group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is proposed for use in artificial liposomes formed from phosphatidyl choline and phosphatidyl glycerol. It is said to be effective in activating human monocytes and destroying tumor cells, but is non-toxic in generally high doses. The compounds of U.S. Pat. No. 4,950,645 and PCT Patent Application WO 91/16347, which have not previously been suggested for use with cellular carriers, are now proposed for use in the present invention.

A preferred adjuvant in the present invention is BCG BCG (bacillus Calmette-Guerin, an attenuated strain of Mycobacterium) and BCG-cell wall skeleton (CWS) may also be used as adjuvants in the invention, with or without trehalose dimycolate. Trehalose dimycolate may be used itself. Azuma et al., (1988) show that trehalose dimycolate administration correlates with augmented resistance to influenza virus infection in mice. Trehalose dimycolate may be prepared as described in U.S. Pat. No. 4,579,945.

BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. Recently developed molecular genetic tools and methods for mycobacteria have provided the means to introduce foreign genes into BCG (Jacobs et al., 1987; Snapper et al., 1988; Husson et al., 1990; Martin et al., 1990). Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE® BCG (Organon Inc., West Orange, N.J.).

In a typical practice of the present invention, cells of Mycobacterium bovis-BCG are grown and harvested by methods known in the art. For example, they may be grown as a surface pellicle on a Sauton medium or in a fermentation vessel containing the dispersed culture in a Dubos medium (Dubos et al., 1947; Rosenthal., 1937). All the cultures are harvested after 14 days incubation at about 37° C. Cells grown as a pellicle are harvested by using a platinum loop whereas those from the fermenter are harvested by centrifugation or tangential-flow filtration. The harvested cells are re-suspended in an aqueous sterile buffer medium. A typical suspension contains from about $2\times10^{10}$ cells/ml to about $2\times10^{12}$ cells/ml. To this bacterial suspension, a sterile solution containing a selected enzyme which will degrade the BCG cell covering material is added. The resultant suspension is agitated such as by stirring to ensure maximal dispersal of the BCG organisms. Thereafter, a more concentrated cell suspension is prepared and the enzyme in the concentrate removed, typically by washing with an aqueous buffer, employing known techniques such as tangential-flow filtration. The enzyme-free cells are adjusted to an optimal immunological concentration with a cryoprotectant solution, after which they are filled into vials, ampoules, etc., and lyophilized, yielding BCG vaccine, which upon reconstitution with water is ready for immunization.

Amphipathic and surface active agents, e.g., saponin and derivatives such as QS21 (Cambridge Biotech), form yet another group of preferred adjuvants for use with the immunogens of the present invention. Nonionic block copolymer surfactants (Rabinovich et al., 1994; Hunter et al., 1991) may also be employed. Oligonucleotides, as described by Yamamoto et al., (1988) are another useful group of adjuvants. Quil A and lentinen complete the currently preferred list of adjuvants. Although each of the agents, and the endotoxins described below, are well-known as adjuvants, these compounds have not been previously incorporated into the membrane of a target cell, as shown herein.

One group of adjuvants preferred for use in the invention are the detoxified endotoxins, such as the refined detoxified endotoxin of U.S. Pat. No. 4,866,034. These refined detoxified endotoxins are effective in producing adjuvant responses in mammals.

The detoxified endotoxins may be combined with other adjuvants to prepare multi-adjuvant-incorporated cells. Combination of detoxified endotoxins with trehalose dimycolate is contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436, 727, 4,436,728 and 4,505,900. Combinations of just CWS and trehalose dimycolate, without detoxified endotoxins, is also envisioned to be useful, as described in U.S. Pat. No. 4,520,019.

One group of adjuvants particularly preferred for use in the present invention are those that can be encoded by DNA or RNA. It is contemplated that such adjuvants may be encoded in a LEE or CEE vector encoding the antigen, or as separate LEE or CEE vectors, or traditional plasmids or other constructs. These nucleic acids encoding the adjuvants can be delivered directly, such as for example with lipids or liposomes. A LEE or CEE encoding antigens might also be formulated with proteinaceous adjuvants in a lipid or liposome.

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

Vaccines may be conventionally administered parenterally, by injection, for example, either subcutaneously, intradermally or intramuscularly. In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies.

L. Immunological Reagents

In certain aspects of the invention, one or more antibodies may be produced to the expressed ORF. These antibodies may be used in various diagnostic or therapeutic applications, described herein below.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

The methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, Pa.); low-dose Cyclophosphamide (CYP; 300 mg/m$^2$) (Johnson/Mead, N.J.), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). cites). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71–74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Alternatively, monoclonal antibody fragments encompassed by the present invention can be synthesized using an automated peptide synthesizer, or by expression of full-length gene or of gene fragments in $E.$ $coli.$ 1. Antibody Conjugates The present invention further provides antibodies to ORF transcribed messages and translated proteins, polypeptides and peptides, generally of the monoclonal type, that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional. immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti-cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody-directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

2. Immunodetection Methods

In still further embodiments, the present invention concerns immunodetection methods for binding, purifying, removing, quantifying and/or otherwise generally detecting biological components such as ORF expressed message(s), protein(s), polypeptide(s) or peptide(s). Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference.

In general, the immunobinding methods include obtaining a sample suspected of containing ORF expressed message and/or protein, polypeptide and/or peptide, and contacting the sample with a first anti-ORF message and/or anti-ORF translated product antibody in accordance with the present invention, as the case may be, under conditions effective to allow the formation of immunocomplexes.

These methods include methods for purifying an ORF message, protein, polypeptide and/or peptide from organelle, cell, tissue or organism's samples. In these instances, the antibody removes the antigenic ORF message, protein, polypeptide and/or peptide component from a sample. The antibody will preferably be linked to a solid support, such as in the form of a column matrix, and the sample suspected of containing the ORF message, protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen, and contact the sample with an antibody against the ORF produced antigen, and then detect and quantify the amount of immune complexes formed under the specific conditions.

In terms of antigen detection, the biological sample analyzed may be any sample that is suspected of containing an antigen, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts are preferred.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any ORF antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional. advantages through the use of a secondary binding ligand such as a second antibody and/or a biotin/avidin ligand binding arrangement, as is known in the art.

The ORF antigen antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The immunodetection methods of the present invention have evident utility in the diagnosis and prognosis of conditions such as various diseases wherein a specific ORF is expressed, such as an viral. ORF of a viral infected cell, tissue or organism; a cancer specific gene product, etc. Here, a biological and/or clinical sample suspected of containing a specific disease associated ORF expression product is used. However, these embodiments also have applications to non-clinical samples, such as in the titering of antigen or antibody samples, for example in the selection of hybridomas.

In the clinical diagnosis and/or monitoring of patients with various forms a disease, such as, for example, cancer, the detection of a cancer specific ORF gene product, and/or an alteration in the levels of a cancer specific gene product, in comparison to the levels in a corresponding biological sample from a normal subject is indicative of a patient with cancer. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive. Of course, the antibodies of the present invention in any immunodetection or therapy known to one of ordinary skill in the art.

a. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the anti-ORF message and/or anti-ORF translated product antibodies of the invention are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another anti-ORF message and/or anti-ORF translated product antibody that is linked to a detectable label. This type of ELISA is a simple "sandwich ELISA". Detection may also be achieved by the addition of a second anti-ORF message and/or anti-ORF translated product antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with the anti-ORF message and/or anti-ORF translated product antibodies of the invention. After binding and/or washing to remove non-specifically bound immune complexes, the bound anti-ORF message and/or anti-ORF translated product antibodies are detected.

Where the initial anti-ORF message and/or anti-ORF translated product antibodies are linked to a detectable label, the immune complexes may be detected directly. Again, the immune complexes may be detected using a second antibody that has binding affinity for the first anti-ORF message and/or anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

b. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25–50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

M. Assays of Gene Expression

Assays may be employed within the scope of the instant invention for determination of the relative efficiency of expression from a LEE or CEE. For example, assays may be used to determine the efficacy of deletion mutants of specific promoter regions in directing expression of operably linked genes. Similarly, one could produce random or site-specific mutants of promoter regions and assay the efficacy of the mutants in the expression of an operably linked gene. Alternatively, assays could be used to determine the function of a promoter region in enhancing gene expression when used in conjunction with various different regulatory elements, enhancers, and exogenous genes.

Gene expression may be determined by measuring the production of RNA, protein or both, or a consequence of RNA protein, polypeptide or peptide production. The gene product (RNA or protein) may be isolated and/or detected by methods well known in the art. Following detection, one may compare the results seen in a given cell line or individual with a statistically significant reference group of non-transformed control cells. Alternatively, one may compare production of RNA or protein products in cell lines transformed with the same gene operably linked to various mutants of a promoter sequence. In this way, it is possible to identify regulatory regions within a novel promoter sequence by their effect on the expression of an operably linked gene.

In certain embodiments, it will be desirable to use genes whose expression is naturally linked to a given promoter or other regulatory element. For example, a prostate specific promoter may be operably linked to a gene that is normally expressed in prostate tissues. Alternatively, marker genes may be used for assaying promoter activity. Using, for example, a selectable marker gene or a specific antibody, one could quantitatively determine the resistance conferred upon a tissue culture cell line or animal cell by a construct comprising the selectable marker gene operably linked to the promoter to be assayed. Alternatively, various tissue culture cell line or animal parts could be exposed to a selective agent and the relative resistance provided in these parts quantified, thereby providing an estimate of the tissue specific expression of the promoter.

Screenable markers constitute another efficient means for quantifying the expression of a given gene. Potentially any screenable marker could be expressed and the marker gene product quantified, thereby providing an estimate of the efficiency with which the promoter directs expression of the gene. Quantification can readily be carried out using either visual means, or, for example, a photon counting device.

A preferred screenable marker gene for use with the current invention is β-glucuronidase (GUS). Detection of GUS activity can be performed histochemically using 5-bromo4-chloro-3-indolyl glucuronide (X-gluc) as the substrate for the GUS enzyme, yielding a blue precipitate inside of cells containing GUS activity. This assay has been described in detail (Jefferson, 1987). The blue coloration can then be visually scored, and estimates of expression efficiency thereby provided. GUS activity also can be determined by immunoblot analysis or a fluorometric GUS specific activity assay (Jefferson, 1987). Other preferred screenable marker genes that could be used with the invention include LUC, LacZ or various GFPs.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Description of Plasmids and Lees

To construct the inventors' standard reporter plasmid, pCMViLUC, the luciferase-encoding LUC+ gene from pGL3-basic (Promega, Inc.) was inserted as an MluI/XbaI fragment into expression vector pCMV-5 (Andersson et al., 1989), and a chimeric intron from pCI (Promega, Inc.) was added as a SacI/EcoRI fragment.

The complete 3.4 kb LEE.LUC was built by PCR®-amplifying the CMVi promoter, luciferase coding sequence, and hGH terminator from plasmid template pCMViLUC by standard protocols (Perkin-Elmer, Inc.). Two standard 20-mer primers were used that correspond to the 5' and 3' ends of the promoter and terminator regions, nucleotide positions 151 and 1590, respectively, of pCMV-5. The LEE components were built by separately PCR®-amplifying the CMVi promoter, a coding sequence, or hGH terminator from plasmid templates by standard protocols (Perkin-Elmer, Inc.). Primers were synthesized with standard phosphoramidites except, when indicated, five dU residues were incorporated every third position 15 bases from the 5' end to cause UDG sensitivity. The 1.1 kb CMVi promoter component was amplified from pCMVi. It includes the CMV immediate early gene promoter from pCMV-5, spanning nucleotide positions 151 to 915, and the chimeric intron sequences of pCI (Promega, Inc.) from position 1063 to 722. The reverse primer for the CMV.LEE begins with a 15 base dU stretch: ACUACUACUACUACU (SEQ ID NO:1), then 18 bases corresponding to the complement of chimeric intron sequences.

The LUC gene was amplified from plasmid template pLUC, from which the CMV promoter and intron had been deleted. Two different LUC products were made, one with (2.26 kb) and one without (1.66 kb) the hGH termination region. Both products included nucleotide positions 85 through 1742 of pGL3-basic and the 2.26 kb fragment extended into the termination sequence of pLUC. The forward primer for both products begins with the dU stretch: AGUAGUAGUAGUAGU (SEQ ID NO:2) then continueD with 18 nucleotides corresponding to the LUC gene. The 5' end of the reverse primer for the 1.66 kb product begins with a 14 base dU region: AUGAUGAUGAUGAU (SEQ ID NO:3), then continues with 18 nucleotides corresponding to the component LUC gene. The standard hGH 3' primer was used. The 0.61 hGH terminator was amplified from pCMV, spenning nucleotides 980 to 1570. The forward primer for the hGH terminator LEE begins with a 14 base dU stretch: AUCAUCAUCAUCAU. The standard hGH 3' primer was used.

Crude PCR® products may be isolated from agarose gels or filtered through Qiaquick membranes (Qiagen, Inc.). To produce 3' overhangs, PCR® products were treated with one to two units of UDG (NEB, Inc.) per µg of DNA for 30 min at 37° C. in reaction buffer (20 mM Tris-HCl pH 8.0, 1 mM EDTA, 1 mM DTT). The enzyme was heat-inactivated, and the samples were extracted and ethanol precipitated. Pellets were resuspended in annealing buffer (20 mM Tris-HCl pH 8.4, 1.5 mM MgCl$_2$) at a concentration of 0.25 µg/ml, melted briefly at 95° C., then transferred to a 72° C. After the addition of 0.5M KCl, samples were slowly cooled to 25° C. to allow annealing.

EXAMPLE 2

Efficient Expression of a Linear Expression Element in Animals

An amplification product was produced containing a cytomegalovirus promoter (CMVi), a luciferase reporter gene (LUC), and the human growth hormone gene terminator (hGH). This in vitro-produced, non-replicating LEE was precipitated onto gold microprojectiles and shot with a gene gun (Sanford et al., 1991) into mouse ears. For comparison, a molar equivalent of the LUC gene with the same promoter and terminator was delivered on a supercoiled plasmid (pCMViLUC), and the skin tissues were assayed for luciferase activity 24 to 36 h later (FIG. 1).

The standard supercoiled LUC plasmid generated an average of 7.3×10⁷ lumens per bombarded ear. Background luminescence from tissue bombarded with empty plasmid (pCMVi) was no higher than untreated tissue or sample blanks.

Reporter gene activity produced from a crude PCR® reaction containing the product that encodes luciferase (LEE.LUC) was 19% of the standard activity. Gel-isolation of the LEE.LUC product before delivery improved subsequent gene activity to 67% of that produced from introduction of the standard plasmid, and a one-step filter purification raised LEE.LUC generated activity to near that of the plasmid (93%). Contaminating template contributed insignificantly to the measured gene expression since introducing a sample that had been treated in exactly the same manner as the filter-purified sample, but without Taq polymerase, led to only 0.5% of the luciferase activity. Primers, unincorporated nucleotides, or electrophoresis contaminants in the unpurified LEE.LUC samples may decrease the efficiency of gene transfection or expression. Since these impurities are easily avoided, subsequent studies were conducted with filter-purified PCR® products.

EXAMPLE 3

Production of Linked Lees

The data reported in Example 2 demonstrate that gene expression levels from a PCR® product encoding a complete gene are similar to that from a conventional plasmid. However, while direct amplification of whole genes will be useful for a number of applications, it will not always be possible to amplify contiguous promoter, ORF, and terminator sequences. For example, most gene screening assays will require fusing a common promoter to a variety of ORFs, or a reporter ORF to a variety of promoters. Screening microbial genes in mammalian cells would require fusing the prokaryotic ORFs to a eukaryotic promoter and terminator. Therefore, an ideal LEE system will typically involve amplification of only an ORF which would then be linked to a set of standard promoter and terminator sequences.

To resolve the above issues, the inventors developed a strategy to produce complementary single-stranded overhangs on the ends of separate PCR® products carrying the ORF, promoter, and terminator sequences. Single-stranded regions of sufficient length anneal and the attached expression components are directly delivered into tissue.

Figure 2:
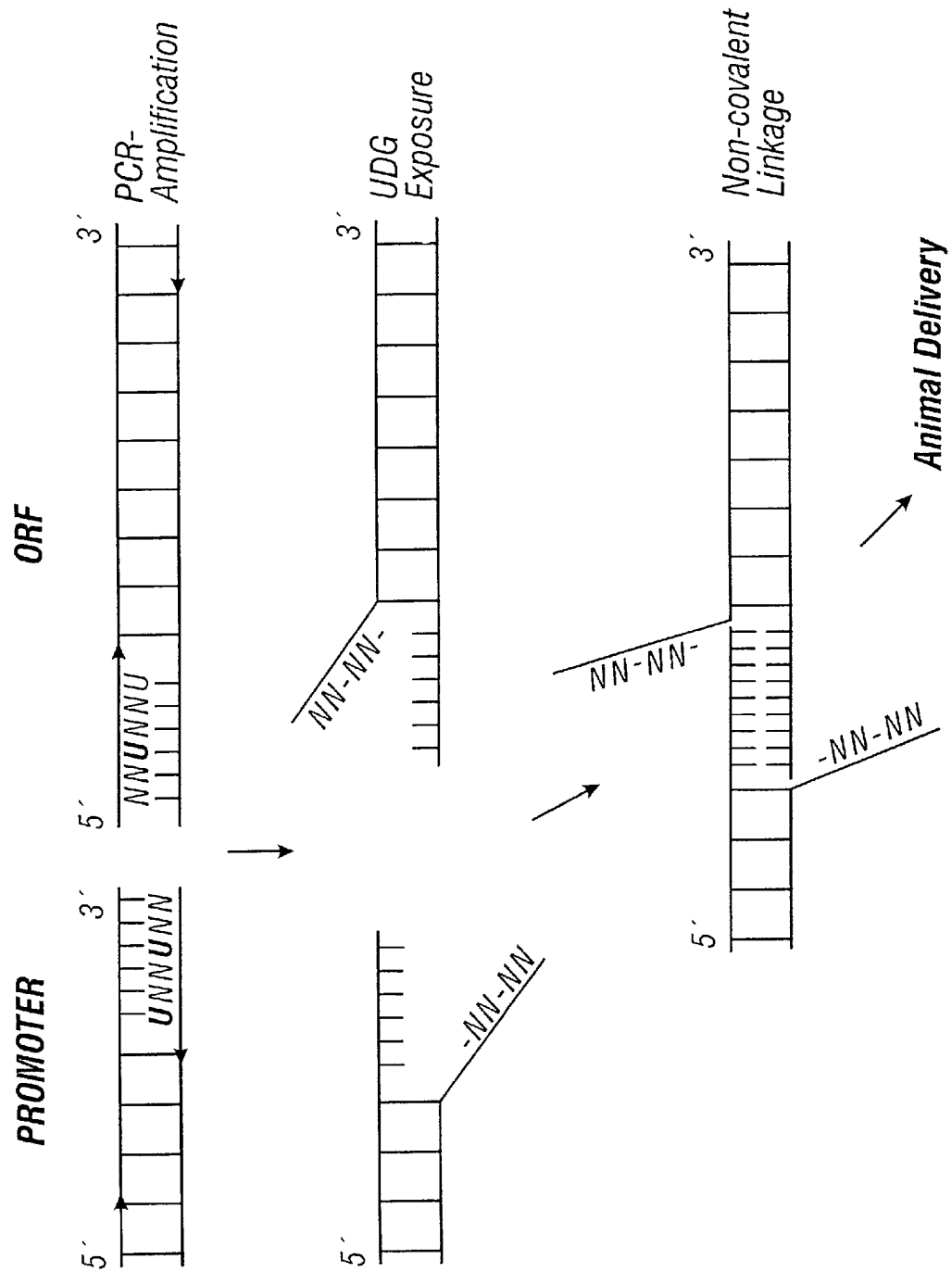
FIG. 2. Cartoon depicting a method for building LEEs from separate genetic components.

A number of methods to create sequence-specific single-stranded overhangs on any PCR® product were investigated. The most efficient procedure was to prime the chain reactions with oligonucleotides that begin with a 12 to 15 base complementary stretch in which deoxyuridines (dU) are incorporated every third position. After amplification, the products were treated with uracil DNA glycosylase (UDG) to excise uracil residues (Nisson et al., 1991). The resulting a basic sites destabilize strand-annealing within the primer regions. The remaining 3' strands are intact and provide complementary overhangs by which the separate PCR® products can link. (FIG. 2).

For example, to build the antigen-expressing LEE.AAT, which is discussed in Example 7, the AAT gene-coding sequence (Andersson et al., 1989) was amplified in cis with the hGH terminator sequence described above, using pCM-ViAAT as template. A standard antigen expression plasmid, pCMViAAT, contains the human AAT gene from pCM-VAAT (Tang et al., 1992) cloned as an EcoRI fragment into pCMVi. The 5' end of the forward primer for the 1.9 kb PCR® product contained dUs: AGUAGUAGUAGUAGU (SEQ ID NO:2) and the 3' terminator primer was standard.

Thus, LEEs can be built by amplifying the ORFs from start to stop codon using DNA as template. The 5' primers may begin with a uracil rich streach such as, for example, AGUAGUAGUAGUAGU (SEQ ID NO:2) then continue with ORF-specific nucleotides retrieved from, for example, the GenBank database. The 3' primers begin with another uracil rich streach, for example, AUGAUGAUGAUGAU (SEQ ID NO:3) then continue with an ORF-specific sequence. These dU ends are compatible for hybridization to the promoter and terminator sequences described above.

An alternate promoter sequence may be built in order to include the other sequences, such as for example, those encoding the secretory leader of tissue plasminogen activator (tPA) protein (Fisher et al., 1985). The PCR® template for this promoter may be, for example, the genetic immunization vector pCMVitPA, which was constructed by inserting the leader sequence as an EcoRI/Bgl2 fragment into pCMVi. Int is contemplated that other changes will be made to make the 3' promoter primer more compatable, such as ACUACUACUACUACU (SEQ ID NO:4) followed by 20 nucleotides corresponding to SEQ ID NO:1, the complement of the tPA leader sequence. Annealing of this alternate promoter to the ORFs will encode the antigens fused to the leader peptide.

Crude PCR® products may be isolated from agarose gels or filtered through Qiaquick membranes (Qiagen, Inc.). To produce 3' overhangs, PCR® products can be treated with one to two units of UDG (NEB, Inc.) per μg of DNA for 30 min at 37° C. in reaction buffer (20 mM Tris-HCl pH 8.0, 1 mM EDTA, 1 mM DTT). The enzyme can be heat-inactivated, and the samples were extracted and ethanol precipitated. Pellets can be resuspended in annealing buffer (20 mM Tris-HCl pH 8.4, 1.5 mM MgCl$_2$) at a concentration of 0.25 μg/ml, melted briefly at 95° C., then transferred to a 72° C. After the addition of 0.5M KCl, samples can be slowly cooled to 25° C. to allow annealing.

LEEs can be prepared for gene-gun delivery by directly adding PCR® products to the gold precipitation reactions without prior annealing. Annealing efficiency can be determined by gel electrophoresis, typically yielding 50%–100% full length products. For calculating reporter and antigen gene doses, LEE annealing may be assumed to be 100%. Therefore all values will reflect expression from a conservatively estimated number of full length LEEs.

EXAMPLE 4

Noncovalently Linked Lees Express In vivo

To determine whether the noncovalently linked LEEs produced according to Example 3 can express genes in vivo, the CMVi promoter and a luciferase reporter gene (including a terminator) were separately amplified using one standard and one dU-containing primer in each reaction. Annealing of the Uracil Deglycosolase (UDG)-treated PCR® products carrying either a CMVi promoter or a LUC gene to form a complete LEE (bi-LEE.LUC) with 1 unit or 2 units of UDG. The two products electrophoresed as expected for 1.1 kb and 2.3 kb fragments. These were incubated with UDG and annealed to form the 3.4 kb expression element bi-LEE.LUC.

Figure 3:
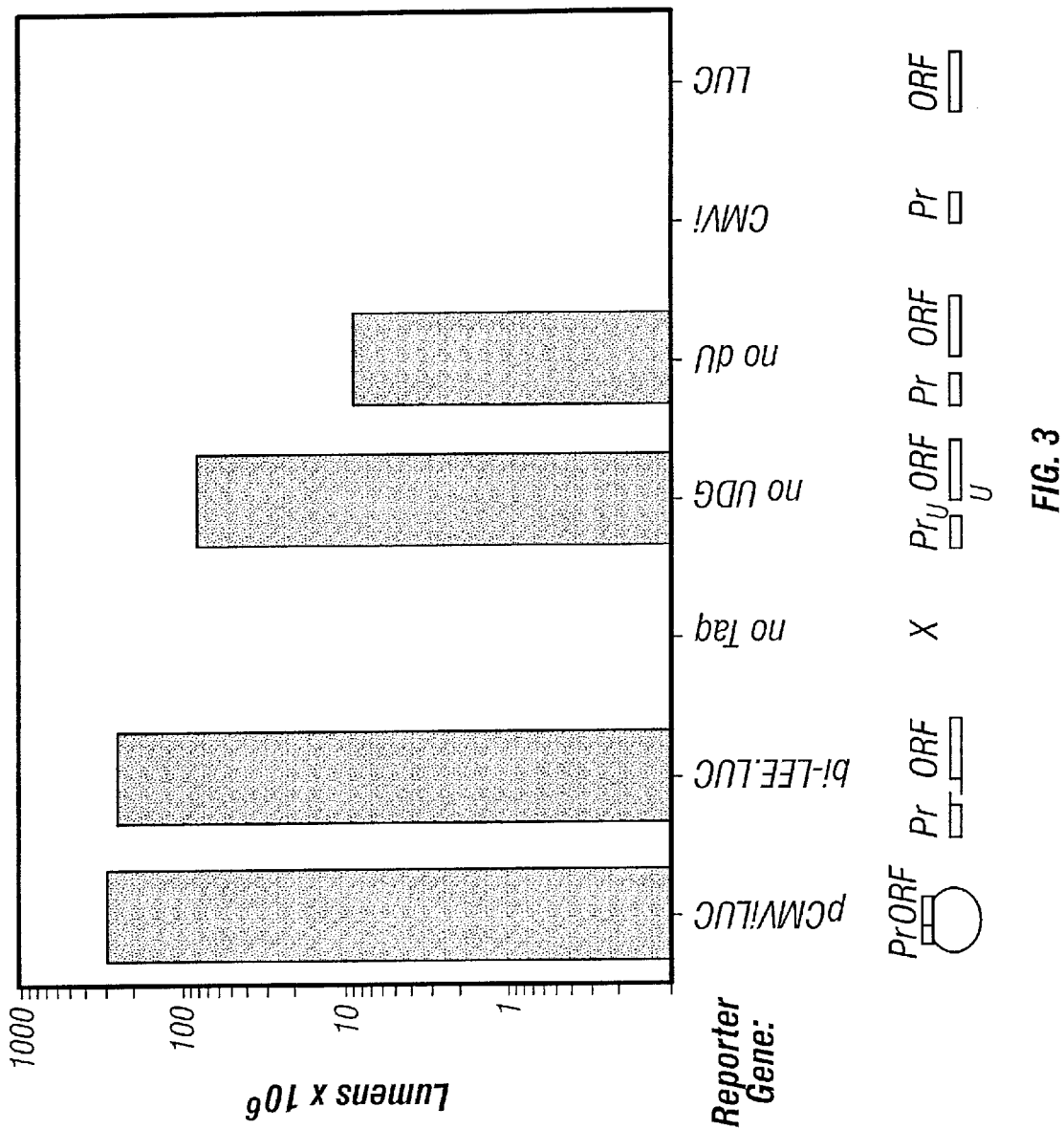
FIG. 3. The noncovalently linked promoter and ORF produce reporter activity. Ears were bombarded with the indicated DNAs, some abbreviations are described in FIG. 1. No UDG=UDG-sensitive products delivered without UDG pre-treatment; no dU=promoter and LUC products amplified with standard primers; CMVi=only promoter product; LUC=only reporter product (topologies of the introduced expression elements are drawn at the bottom of FIG. 3); Pr=promoter; ORF=open reading frame, X=no product. Activities are reported as described in FIG. 1.

Reporter genes were introduced into the ears of Swiss-Webster mice with a gene gun (Sanford et al., 1991) (built by Rumsey-Loomis, Ithaca, NY) or with a needle into the tibialis anterior muscle (Wolff et al., 1990). An equal gene-dose of luciferase reporter gene was borne on LEE (3.4 kb) and plasmid (6.7 kb). Ear and muscle tissues were harvested one to two days later and assayed for activity with standard reagents (Promega, Inc.). Readouts were normalized to 1.0 µg plasmid and 0.5 µg LEE. Protein determinations done on lysates in several studies showed that any group of muscles, or group of ears, contained similar protein levels but the total amount of protein extracted from muscle samples was generally twice that extracted from ear samples. However for simplicity, activities are reported as total lumens per tissue, which may underestimate expression per cell from gene-gun delivered samples. The graph in FIG. 3 shows that biolistic introduction of the unligated sample into mouse skin produced 85% of the luciferase activity produced from delivery of an equivalent gene-dose of the LUC plasmid, assuming complete annealing of the LEE.

Background expression due to PCR®-template contamination was prevented by using plasmid templates that were LUC-less or promoter-less to amplify the promoter or LUC gene, respectively. As expected, control samples without polymerase showed no reporter activity. Results indicated that attachment of a promoter and ORF by simple overhang-hybridization enables plasmid-like levels of gene delivery and expression of an LEE in the animal.

To test the importance of fragment annealing for generating this gene expression, the dU primed PCR® products were introduced without being pre-treated with UDG. Surprisingly, these LEEs produced 29% of the standard-plasmid reporter-gene activity. The relatively high level of gene expression suggested that exposure to endogenous murine UDG (Nisson et al., 1991) enables in vivo annealing and sticky-end ligation.

The promoter and reporter gene were also amplified with standard primers that did not contain dUs. Introduction of these blunt-ended PCR® fragments produced low but detectable levels of luciferase activity, presumably due to in vivo blunt-end ligation. Either product delivered into separate animals produced no reporter activity. (FIG. 3).

EXAMPLE 5

Production of Lees with Terminator Sequences

Figure 4:
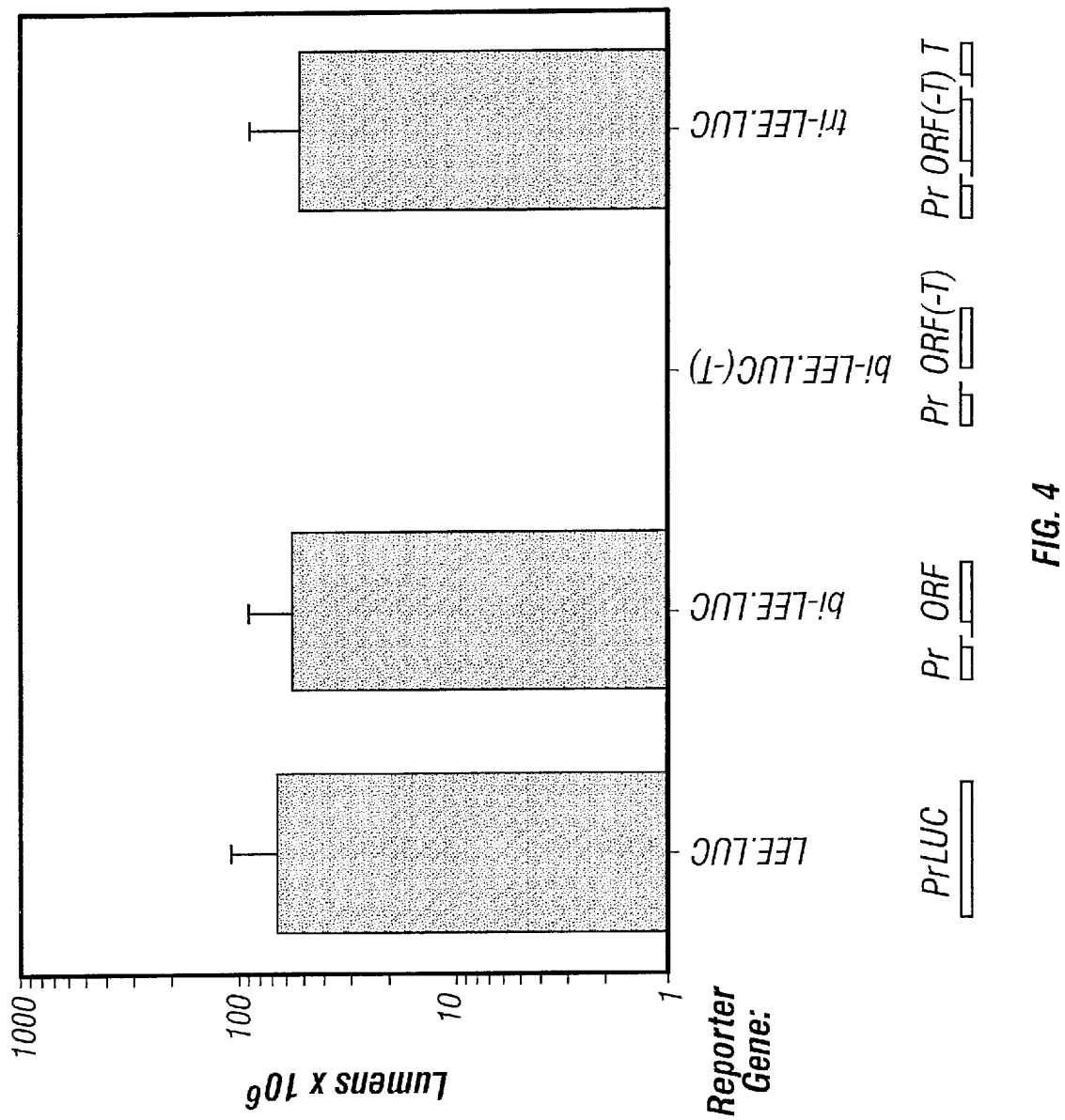
FIG. 4. A trimolecular LEE efficiently produces luciferase gene activity in vivo. bi-LEE.LUC(-T)=two linked PCR® products carrying promoter and LUC without a terminator; tri-LEE.LUC=three linked PCR® products carrying promoter, ORF, and terminator. Some abbreviations are described in FIG. 3. Topologies of the introduced expression elements are drawn at the bottom of FIG. 4. ORF(-T)=LUC ORF without terminator; T=terminator. Activities are reported as described in FIG. 1.

Many applications of the LEE technique would require attaching both a new promoter and a terminator to a particular coding sequence, for example, in cases where a native terminator is not included with the ORF. Therefore, the practicality of such a linkage was assessed. A three-component LEE expressing luciferase (tri-LEE.LUC) was prepared from PCR® products that separately carried the CMVi promoter, LUC coding sequence, and hGH terminator. The dU primed amplification products were UDG treated, annealed by strand-hybridization without ligase, and immediately shot into mice. The data in FIG. 4 show that the level of luciferase activity generated by this triple arrangement was 77% of that from a single PCR® product carrying all three components, whereas, delivery of an LEE composed of a promoter and ORF but not a terminator produces negligible gene activity. This is impressive since the yield of fully annealed product would presumably decrease as the number of required interactions increase.

EXAMPLE 6

Production of Cees

A circular expression element (CEE) was engineered to simplify these gene vehicles. This dU-primed PCR® product carries a divergently-oriented promoter and terminator at its ends so that this element can be linked to an ORF to add both expression sequences to an ORF. The resulting circular element is not a plasmid since it is nonreplicative and contains only the sequences necessary for the desired gene expression. Other genes in CEEs, like LEEs, are effectively delivered in vivo to yield reporter gene activity. In particular embodiments there is not excess additional superfluous plasmid backbone sequences comprising a CEE. In particular aspects the CEE is produced by PCR® amplification.

EXAMPLE 7

Lees Introduced into Animals are Expressed and Result in Antibody Expression

Figure 5:
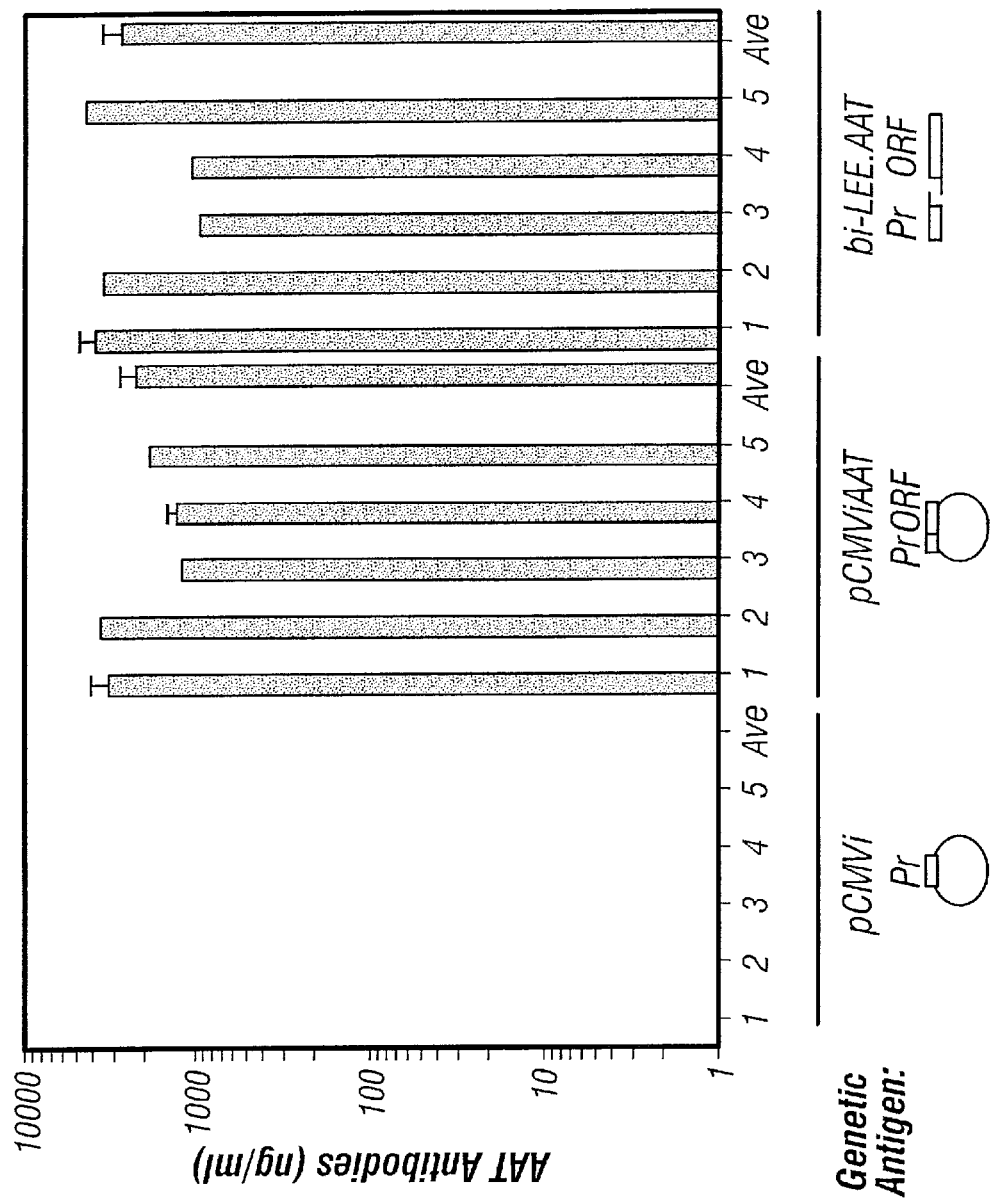
FIG. 5. Introduction of a bimolecular LEE encoding AAT generates specific antibodies in mice at titers comparable to that produced from a plasmid encoding this test antigen. Mice were biolistically immunized with either 1 µg of pCMVi, 1 µg pCMViAAT, or 0.5 µg bi-LEE.AAT. Sera were collected and tested by ELISA at 1:1000 dilution. Topologies of the introduced DNAs are drawn below the graph. Individual and group averages are plotted with standard errors.

To test the ability of these linear DNAs to raise an immune response, a LEE was designed to express human α-1 antitrypsin (AAT) by noncovalently linking the PCR®-amplified CMVi promoter to the AAT ORF (with terminator). The antibody levels presented in FIG. 5 show that introduction into mouse skin of either the bimolecular LEE (bi-LEE.AAT) or a molar-equivalent of a standard supercoiled plasmid (pCMViAAT) produced AAT-specific responses. Antibody titers in the two AAT-gene vaccinated groups were similar and all five mice per group responded. A control group vaccinated with empty plasmid did not produce a response.

Groups of five BALB/c mice were vaccinated with the antigen gene AAT on a plasmid or LEE, or with a control plasmid. One µg pCMViAAT, 0.5 µg bi-LEE.AAT or 1 µg pCMVi were biolistically delivered into the ears. Animals were boosted at week two and bled four months later without further boosts. Sera from groups were individually collected and tested in duplicate for AAT-specific antibodies by ELISA using standard protocols (Harlow and Lane, 1988). Primary sera were diluted 1:500, 1:1000, and 1:2000 in TBS-T (Harlow and Lane, 1988) and 2.5% BSA. Data in FIG. 5 are reported from sera diluted 1:1000. Concentrations of AAT-specific IgGs in sera were determined by serially diluting a monoclonal anti-AAT antibody (CalBiochem, Inc.).

EXAMPLE 8

Genetic Immunizations Employing Lees and Cees

LEE and CEE methods are well-tailored for genetic immunizations (Tang et al., 1992). Each ORF of a pathogen could be attached to eukaryotic expression sequences, introduced into a host, and tested as a protective antigen. In addition, any ORF could be introduced into mice or rabbits to produce antibodies for analytical purposes (Barry et al., 1994).

To directly demonstrate the potentials of this protocol for producing useful antibody reagents or for the development of an important vaccine, LEEs may be built to express pathogen ORFs. ORFs can be amplified from genomic DNA with dU primers, UDG-treated and linked to a mammalian promoter and terminator as described. Each LEE can be used to vaccinate an organism, such as sets of BALB/c mice; a plasmid encoding murine GMCSF can be included as a genetic adjuvant.

The LEEs expressing ORFs can be used to biolistically immunize an organism, such as for example, BALB/c mice. 2 µg of each LEE encoding an ORF can be shot into the ears of two mice. Each set of animals can be boosted at weeks three and five then bled twelve days later.

Sera from immunized and non-immunized mice can be subsequently analyzed. A standard immunoblot can be used to analyze the sera against total cell lysates of the ORF's originating organism (20 µg) gel-fractionated in 12.5% SDS-PAGE (Harlow and Lane, 1988) and the sera from mice that were vaccinated biolistically with 2 µg of ORF can be analyzed by immunoblot. Sera can be diluted, for example, 1:300 in TBS-T and 5% dry milk. HRP-conjugated rabbit antimouse IgG+IgM (Pierce, Inc.), or other suitable secondary antibody can be diluted, for example, in 1:2500 in TBS-T and 5% milk and used as a secondary antibody for chemiluminescent (Renaissance, NEN, Inc.) detection. Unimmunized but age matched mice are expected to show no specific reactivities.

Vaccination with the LEEs are expected to generate antibodies in the animals that recognized specific polypeptides. It is expected that unpropagated, unligated PCR® products can be used to produce specific humoral immune responses against relevant pathogens.

It is contemplated that LEEs can be used as gene vaccines to raise antibodies against encoded eukaryotic or prokaryotic antigens. Sufficient gene expression is expected to be achieved in order to stimulate humoral responses.

EXAMPLE 9

Expression of Lees and Cees in Tissue Culture

The LEE and CEE technology may also be used for cell culture transfections. The performance of the reporter gene LEEs was tested in PEA10 mouse fibroblasts. For cell culture transfections, the same luciferase reporter gene was delivered into murine, BALB/c-derived fibroblast cells (PEA10) with a chamber gene-gun (Roomsey-Loomis, Ithaca, N.Y.). Plates of $10^6$ cells were shot in triplicate with equal gene-doses of LEE.LUC or LUC plasmid. Cells were harvested into lysis buffer 18 h later. Total protein concentrations were determined (Pierce, Inc.) for each sample. Luciferase activity was measured and calculated as lumens per mg lysate.

Figure 6:
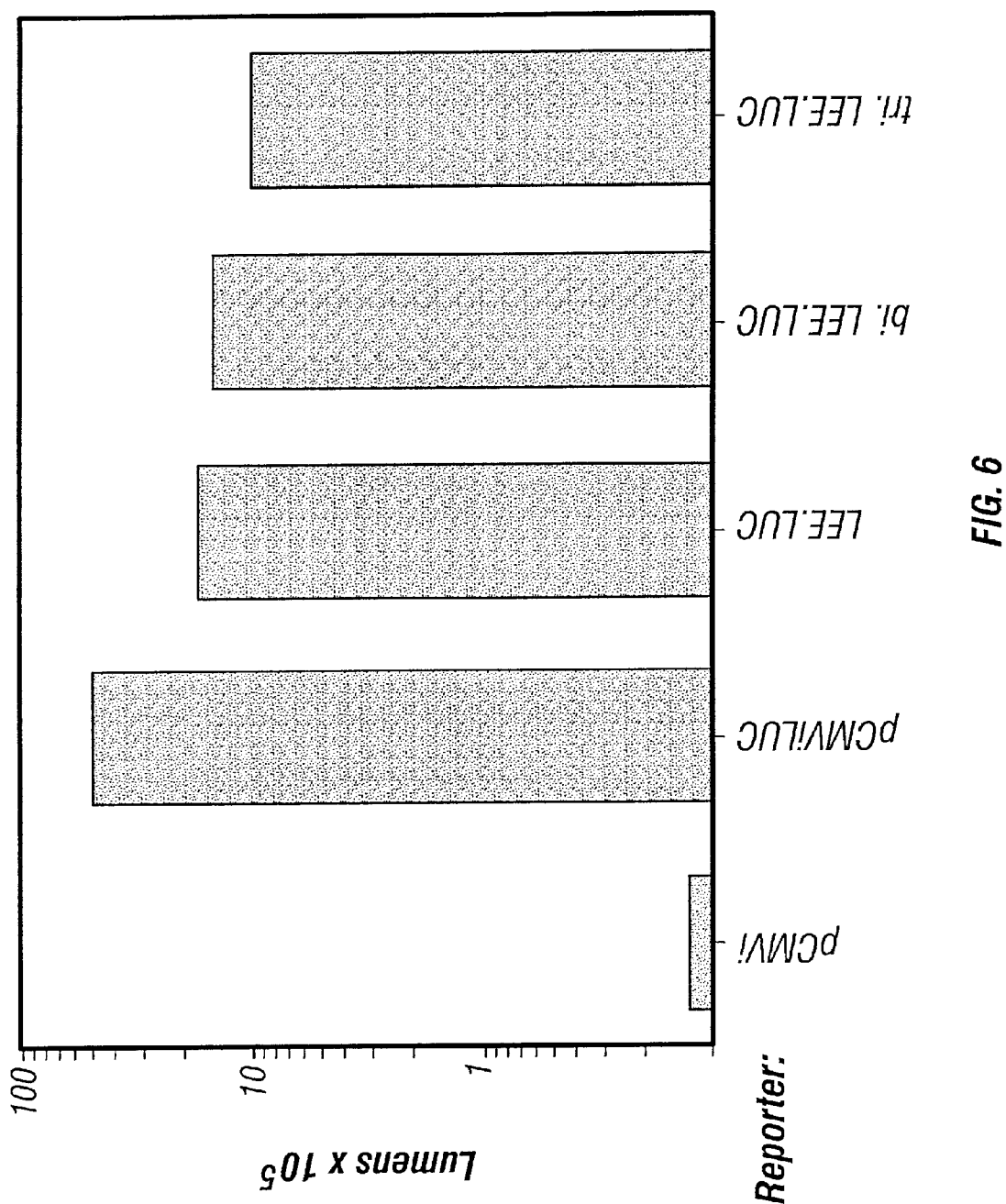
FIG. 6. LEE-encoded compared with plasmid-encoded gene expression in tissue culture. Plasmid pCMVi is the empty plasmid, pCMViLUC is the standard plasmid encoding luciferase (LUC), and the LEE.LUC DNAs are the linear expression elements.

The standard pCMViLUC plasmid produced $4.8 \times 10^6$ lumens per milligram of cell lysate while the empty pCMVi plasmid led to no luminescence above sample blanks. (FIG. 6) Luciferase activity generated by the full length LEE.LUC PCR® product was 35% of the standard plasmid. The linked biLEE.LUC and triLEE.LUC products expressed 31% and 21%, respectively, of the plasmid-encoded reporter gene activity. In parallel, mice ears were transfected with the same preparations of either pCMViLUC or full length LEE.LUC and assayed 18 h later. Luciferase activity produced by the LEE was 34% of the standard plasmid. These somewhat lower LEE expression levels both in vitro and in vivo may be a result of a dirtier LEE preparation of the shorter time point assayed. Nonetheless, these results demonstrate a direct correlation between the gene expression levels produced by LEEs transfected into cell cultures with those produced by their transfection into animals.

EXAMPLE 10

Utilization of Lees and Cees to Functionally Screen Viral Genes

LEEs or CEEs can be used to functionally screen a genome for a gene or gene fragment that encodes a product with any activity or indirectly causes an activity that can be assayed. For example, all the open reading frames (ORFs) of a sequenced genome can be PCR-amplified with dU-containing primers directed to the coding sequence endpoints (translation start and stop codons). These ORFs can be linked to promoter- and terminator-containing PCR products as described earlier to create a LEE library. The library can be split into sub-libraries for screening. The number of LEEs per sublibrary and the total number of sublibraries can be varied to accommodate the assay conditions. DNA corresponding to each LEE sublibrary can be delivered biolistically into tissue cultures or into the skin of animals. Transient gene expression, physiological activities and effects, or immune activities and responses could be assayed. Positively scoring sublibraries could be further split in order to test less complex sublibraries, reiteratively, until a single LEE or set of LEEs is identified.

For example, LEEs can be used in the functional screening of viral genes for accumulation of dendritic cells in skin. Individual viral genes can be amplified by polymerase chain reaction (PCR®) using dU-containing primers. Groups composed of 8–10 PCR® products can be mixed with, for example, CMV promoter and hGH terminator sequences amplified with compatible dU-flanks. After treatment with UDG and annealing, the DNA can be precipitated onto gold particles and introduced into skin of mice with the gene gun. After 4 days, the skin can be harvested, and thin sections prepared and stained for the presence of dendritic cells with anti-$1^a$ antibody. An experimental group and a luciferase would not be expected to show a net accumulation of dendritic cells, alongside experimental group X that shows a net accumulation of dendritic cells in the area surrounding the gold particles. Group X can be further split into 10 groups of a single LEE each, these can be introduced into the skin of mice. This enabled a single LEE, expressing one viral ORF to be identified that causes denditic cell recruitment.

EXAMPLE 11

Methods of Employing Lees and Cees to Produce Vaccines

Each pathogen ORF can be generated, annealed to a mammalian promoter and terminator then directly introduced into a test animal as a vaccine. The linear expression elements (LEEs) can be screened individually or in pools. With this method it is envisioned that all the genes of a pathogen can be introduced as genetic vaccines into animals in a matter of days. The animals can be subsequently challenged with pathogen to determine which genes protect against disease. Isolating individual LEEs from protective pools can be conducted as previously described for plasmid libraries (Barry et al., 1995).

In a preferred embodiment, the ORFs of a pathogen are amplified by PCR® for expression by LEEs. Such ORFs may be from known gene sequences deposited with a genetic database, such as for example, the National Center for Biotechnology Information's Genbank and GenPept databases (http://www.ncbi.nlm.nih.gov). The coding regions for these known genes may be amplified and/or expressed using the techniques disclosed herein. Additionally, genes may be amplified using LEEs from a commercially available genetic library specific to a particular pathogen. Or a genetic library specific to one or more pathogens may be prepared, for genomic or cDNA sequence, as would be known to one of ordinary skill in the art (Sambrook et al. 1989). The genes could also be chemically synthesized as linear elements for direct introduction into animals.

A typical procedure would be to synthesize oligonucleotides for the amplification of each gene in a sequenced genome. These oligos would be designed such that they would be used to create LEEs or CEEs as described. ORFs of each gene would be PCR® amplified and the CMV promoter and human growth hormone terminator linked as described. The LEEs could be pooled in groups of ~50, for example, and introduced into the skin by a gene gun or injected with a needle into the test animal. These animals would receive one boost ~3 weeks later of the same DNA and then challenged with the pathogen some time after this. If a group of animals showed resistance to infection, the ~50 genes in that pool would be tested individually or in smaller groups to isolate the ones responsible for protection. If the thousands of genes of the pathogen were cloned by conventional practice, the creation of the pools for screening would have taken months as opposed to a week using LEEs or CEEs.

If the genome sequence was not available, the genome could be subjected to random amplification with dU adapter oligos. These randomly amplified fragments would be linked to the CMV promoter and terminator as before and then pooled for testing as vaccines. Only ~⅙th of the fragments would encode real ORFs.

It is envisioned that LEE technology should permit the rapid screening of all the genomes of pathogens for vaccine candidates.

For example, LEE technology was used to generate random LEE libraries from pathogen genomes designed for the subsequent screening of genes and gene fragments for vaccine candidates. No sequence database is necessary. Instead of using dU-containing primers directed to known ORFs, dU-containing random primers were used. Random LEE libraries have been made from the genomes of Herpes Simplex Virus (a large virus) and Mycoplasma pulmonis (bacteria), or a parasite. The genomic representation of the LEE libraries appears to be broad as measured by the high complexity of the PCR products. The genetic representation was sampled by the successful amplification of a number of known gene fragments from the libraries. Although only ⅙th of the LEEs would properly express a coding region, due to frame and orientation considerations, the ease of production means that very large complexity libraries could be generated. Genomically complete libraries could be generated even from large pathogenic genomes such as parasites for vaccine screening.

EXAMPLE 12

Methods of Lees and Cees to Develop Immunological Reagents

The LEE/CEE approach could be used to rapidly produce immunological reagents such as antibodies. In a representative example, the ORF of one or more genes or portions of genes would be PCR® amplified or chemically synthesized with adapter sequences such that it would attach to a promoter and terminator. These LEEs would then be directly introduced in to an animal to create an immune response to the encoded gene product, for example antibodies. These antibodies could be used directly for research purposes to study that particular gene, for example, which genes are expressed in a particular stage of a pathogen to create vaccine candidates. This procedure could also be used to discover antibodies or other immunological reagents that are useful in diagnostic procedures or have therapeutic value. Since it is very easy to create LEEs and immunize animals with them to create an immune response, it should be possible to rapidly screen many genomes for production of immunologically useful reagents.

LEEs and CEEs can be used in developing immunological reagents for vaccine identification. LEEs and CEEs can be used to produce antibodies to an ORF. Antibodies to all a pathogen's ORFs can be produced, then used to probe pathogen-infected tissue by immunohistochemistry to elucidate which proteins are present in a particular tissue at any pathogen stage-of-interest. Identified gene products are excellent vaccine candidates or drug targets.

In a non-limiting example, useful immunological reagents were generated by LEE technology for the identification of vaccine candidates against the parasite Plasmodium falciparum, the etiological agent of Malaria. A family of diverse genes, called Rifins, with predicted cell-surface localizations was identified following the sequencing of the first chromosome from Plasmodium. Gene coding regions from 16 Rifins were PCR-amplified, linked to mammalian promoter and terminator, then used as inocula to vaccinate groups of CD1 mice for anti-Rifin antibody production. Sera from blood samples were used to probe liver-tissue samples from Plasmodia-infected mice using immunofluorescence assays. From the 16 randomly chosen probes, three positives were found. This demonstrates that the LEE inoculum used to generate the positive sera encodes a protein that exists in the liver-stage disease. Since the presence of these proteins in the liver makes them likely vaccine candidates, the LEE screen may have dramatically streamlined the search for candidates.

In another non-limiting example, a LEE ORF library has been made that encodes all the ORFs of Herpes Simplex Virus (HSV). The genomic and genetic representations have been tested as described. Each LEE has been delivered into a pair of CDI mice for antibody production against the LEE-encoded gene product. Sera will be harvested from the animals to obtain a complete repertoire of HSV antibodies. This type of reagent set will be useful for both clinical and research applications such as proteomics. Similar LEE or CEE libraries could be generated from other genomes of interest.

EXAMPLE 13

Methods of Using Lee and Cee Technology to Screen for Promoter Function

By reversing the variable and constant portions of an LEE/CEE it should be possible to screen for a particular promoter or other regulatory functions. For example, the promoters of many sequenced genes could be PCR® amplified such that they are LEE elements and attached to a constant reporter (e.g., GFP, Luc, B-gal.) ORF. These LEEs could then be shot into, for example, brain sections, and these sections then assayed for which LEE or group of LEEs produced reporter gene product in a particular cell type, e.g., neurons. In this way, the cell specific regulation pattern of any promoter could be determined readily, or large numbers of promoters assayed for expression in particular cell types.

EXAMPLE 14

Use of Lee and Cee Technology to Test for Biological Function of ORFS

In another application, the genes of a virus can be transformed into LEEs, and these put, for example, in 26 groups of 8–10 LEEs. The groups can be shot into the adominal skin of mice, and the skin observed one day later for the number of dendritic cells in the bombarded area. In this way, a group of genes that affected dendritic cell migration can be identified. By using the LEEs, this screening could be accomplished in days, where if conventional cloning had been relied on to isolate the large number of genes in a viral genome, it is expected to take months. Other immune related and unrelated biological activities could be screened such cytokine production or enzyme production.

It is envisioned that it should be possible to screen for an assayable biological function of gene products by directly introducing LEEs/CEEs into organisms, tissue sections or cells. By direct observation of effects on particular cell types versus other cell types, it should be possible to efficiently isolate proteins that have cell specific effects.

EXAMPLE 15

Use of LEES/CEES to Screen Gene Products in Cell-free Systems

It would be very easy to attach an ORF or many ORFs from a genome or other sequence database to a promoter which facilitates in vitro transcription and translation in a cell-free system. Such a construct, for example, with the T7 polymerase promoter, could be used to rapidly produce proteins corresponding to many different genes. This protein could be radioactively or otherwise tagged. These tagged proteins could then be purified or directly screened for those that had a particular function, for example, were able to bind to another particular protein or drug or even that had a particular enzyme activity. This application of the LEE/CEE technology could greatly enhance the proteomic effort, that is, to screen all the proteins of genomes for particular functions or uses.

A particular example of using LEE expressed gene products that are in vitro produced is for the isolation of antibodies or antibody-like molecules. Antibodies are key tools for proteomic analyses. Complete repertoires of antibodies that bind all the proteins of an organism are highly desirable. In a high throughput fashion, LEE's could be synthesized in vitro, products purified then used to fish out, for example, reactive single-chain antibodies expressed within a single-chain-antibody phagemid library. The diversity within the artificial antibody library is much greater than possible in animals, and the time required for the experiment is considerably shorter, requiring no animals.

EXAMPLE 16

Expression of LEES/CEES in Plants

The LEE and CEE technology may also be used for expression of genes in plant protoplasts and whole plants. For example, the strong 35S promoter sequence from Cauliflower Mosaic Virus (CaMV) could be PCR-amplified, as described earlier, with a standard 5'-end primer and a dU-containing primer at its 3' end. The plant reporter gene beta-glucuronidase (GUS) could be amplified with two dU-containing primers. The efficient termination sequence from the nopaline synthetase (NOS) could be amplified with a dU-containing 5' end primer and a standard 3' end primer. UDG treatment would yield single-stranded ends that could anneal that to form a fully functional GUS gene expression unit. The LEE can be precipitated on gold microparticles and delivered with a gene gun into plant cells, tissue, or whole samples. A standard GUS reporter assay will determine gene expression (Jefferson et. al. (1987) EMBO J., pp3901–3907).

EXAMPLE 17

Use of LEES/CEES to Test Plant ORFS for Biological Functions of Interest

The same amplification procedure described in example 16 can be used to generate a LEE that expresses any plant gene of unknown or putative function. Plant-transformation will enable very fast analysis of in vivo gene function. Plant genomes are being sequenced, such as Arabidopsis, and this is identifying new ORFs without know functions. Many times these ORFs have sequence similarity to genes with known functions. The activities of the possible homologues can be quickly tested by constructing LEEs that encode the new ORFs then assaying them in vitro or in vivo for the supposed activity.

LEEs with plant ORFs could be constructed and introduced into plant tissue directly to screen for anything that could be screened for as a local or individual cell trait, or introduce the LEE into cell cultures and screen for cells that display individual trait like disease or herbicide resistance; or shoot all ORFs into plant cells to generate individual transgenic plants to screen for any trait including whole plant features, such as for example, yield or drought resistance.

In particular, the LEE technology could be used to screen plant open-reading frames for useful biological functions. For example, the commonly used 35S promoter or other plant promoters could be PCR amplified with ends that could anneal with the overhangs of the PCR products of each ORF. In the same manner the 3' ends of the ORF may be designed to anneal with a common plant terminator sequence, for example the nopaline synthetase (NOS) termination sequence. These ORFs could be screened for useful functions by introducing them directly into plants or into plant cell cultures. For example the ORFs could be introduced into cell cultures and which were then challenged by a pathogen to screen for ORFs that confer resistance to infection, the ORFs could be screened for ones that conferred protection against herbicides, or the LEE ORFs could be introduced into cells to produce callus and subsequently transgenic plants to then screen for effects on yield, disease resistance, cold or heat resistance, stature, daylenght response, or nutritional trait. In this case the LEE would be co-introduced with a selectable marker or with a selectable trait, for example kanamycin resistance, incorporated into the LEE.

EXAMPLE 18 use of LEES/CEES to Test Plant Promoters

A plant reporter gene as described above can be linked to different promoters, delivered into plants, then tested for tissue or stage-specific activity, or for enhanced promoter activity. In could desirable to express a gene normally expressed in one tissue in a different tissue, or to increase the expression of an endogenous gene. For example pathogens can often infect one but not another tissue. If the gene enabling the resistance of one tissue can be identified then engineered with a promoter expressed in the sensitive tissue, then plant protection may be achieved. Increasing the expression of a gene related to fragrance or color may improve the value of a flowering plant.

All predicted or suspected promoters from a plant could be linked to a reporter gene (for example GUS) and terminator and introduced into the whole plant or tissues, cell cultures or cells to make transgenic plants. The activity of the promoters could then be assayed for useful traits. For example, all the promoters could be linked to GUS by LEE and introduced into roots to find promoters that express preferentially and strongly in roots. Or the promoter-GUS LEEs could be introduced into plant cell cultures and the cells exposed to an enviromental agent (for example, heat, cold, salt, light, herbicides) to determine which promoters respond to which stimuli. Alternatively, transgenic plants could be generated using LEEs as described above where the promoters were linked to a particular ORF and the transgenic plants screened for a desired trait. For example, all promoters could be linked to a heat-shock protein and the resulting transgenic plants screened for heat tolerance. The ORFs or promoters sceeened in plants could be from one plant species screened in another. For example all the ORF of a disease resistant plant could be screened in a susceptible plant. The ORFs or promoters could be from non-plants and transfected into plants.

EXAMPLE 19

Use of LEES/CEES to Generate Plant Libraries for the Functional Screening of Genes or ORFS of Interest LEE libraries can be generated that encode plant genes, gene fragments, or ORFs. These can be transformed as groups into plants to screen for an activity of interest, including protection from plant pathogens. Positively scoring groups can be reduced as described earlier until single ORFs with the activity of interest are isolated. If the plant genomic sequence is not available, random plant libraries could also be generated and tested. For example, one plant species may be resistant to infection from a pathogen. A distinct species, perhaps related but to necessarily related, may be used in crops but is pathogen-sensitive. It would be possible to prepare a LEE library corresponding to all the ORFs of the resistant plant then deliver them in groups into the sensitive plant species. Pathogenic challenge of the normally sensitive plants would identify plants that express the foreign resistance gene(s). Sibbing and further screening could isolate single ORFs.

EXAMPLE 20

Expression of LEES/CEES in Brain or Other Tissue Sections

LEEs could be delivered into live tissue sections such as rat brain slices. Many different promoters could be linked to a reporter gene and terminator. Comparison of reporter activity in the tissue of interest, such as brain, to a control tissue would quickly identify tissue-specific promoters. Alternatively, promoters could be left attached to their natural genes, delivered as LEEs, and tissue-specific expression could be asssesed by visualizing the LEE-encoded gene-products with specific antibodies. As another application, the intracellular localization of the encoded gene product could be determined by linking a gene of interest to a standard promoter, such as CMV, then visualizing the LEE-encoded product by imunohistochemistry.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbondanzo et al., Am J Clin Pathol. 93(5):698–702, 1990.
Abbondanzo et al., Am J Pediatr Hematol Oncol. 12(4):480–9, 1990.
Abdullah et al., *Biotechnology*, 4:1087, 1986.
Abel et al., *Science*, 232:738–743, 1986.
Allred et al., Arch Surg. 125(1):107–13, 1990.
Andersson et al., "Cloning structure and expression of the mitochondrial cytochrome P-450 sterol 26-hydroxylase, A bile acid biosynthetic enzyme," *J. Biol. Chem.*, 264:8222–8229, 1989.
Atherton et al., Biol. of Reproduction, 32, 155–171, 1985.
Barkai-Golan et al., *Arch. Microbiol.*, 116:119–124, 1978.
Barry et al., "Production of monoclonal antibodies by genetic immunization," *Biotech.*, 16:616–620, 1994.
Barry et al., "Protection against mycoplasma infection using expression library immunization," *Nature*, 377:632–635, 1995.
Bates, "Genetic transformation of plants by protoplast electroporation," *Mol Biotechnol.*, 2(2):135–145, 1994.
Battraw and Hall, "Stable transformation of sorghum-bicolor protoplasts with chimeric neomycin phosphotransferase II and beta glucuronidase genes," *Theor. App. Genet.*, 82(2):161–168, 1991.
Becker et al., "Fertile transgenic wheat from microprojectile bombardment of scutellar tissue," *Plant J.*, 5(2):299–307, 1994.
Berberian et al., Science, 261:1588–1591, 1993.
Bernal-Lugo and Leopold, *Plant Physiol.*, 98:1207–1210, 1992.
Berzal-Herranz et al., *Genes and Devel.*, 6:129–134, 1992.
Bhattacharjee; An; Gupta, *J. Plant Bioch. and Biotech.* 6, (2):69–73. 1997.
Blackman et al., *Plant Physiol.*, 100:225–230, 1992.
Bol et al., *Annu. Rev. Phytopath.*, 28:113–138, 1990.
Bower et al., *The Plant Journal.*, 2:409–416. 1992.
Bowler et al., *Ann Rev. Plant Physiol.*, 43:83–116, 1992.
Branson and Guss, *Proceedings North Central Branch Entomological Society of America*, 27:91–95, 1972.
Broakaert et al., *Science*, 245:1100–1102, 1989.
Brown et al., *J Immunol Methods.* 12;130(1):111–121, 1990.
Buising and Benbow, "Molecular analysis of transgenic plants generated by microprojectile bombardment: effect of petunia transformation booster sequence," *Mol. Gen. Genet.*, 243:71–81, 1994.
Buttrick et al., "Behavior of genes directly injected into the rat heart in vivo, *Circulation Res.* 70:193–198, 1992.
Callis et al., *Genes Dev.*, 1:1183–1200, 1987.
Campbell (ed.), *In: Avermectin and Abamectin*, 1989.
Casas et al., "Transgenic sorghum plants via microprojectile bombardment," *Proc. Natl. Acad. Sci. USA*, 90(23):11212–11216, 1993.
Cech et al., *Cell*, 27:487–496, 1981.
Chen and Okayama, "High-efficiency transformation of mammalian cells by plasmid DNA," *Mol. Cell. Biol.* 7:2745–2752, 1987.
Chowrira et al., "Four ribose 2'-hydroxyl groups essential for catalytic function of the hairpin ribozyme." *J Biol Chem.*, 268:19458–19462, 1993.

Chowrira et al., *J. Biol. Chem.,* 269:25856–25864, 1994.
Christou et al., *Proc. Nat'l Acad. Sci. USA,* 84(12):3962–3966, 1987.
Cleary et al., Trends Microbiol., 4:131–136, 1994.
Cotten et al., "High efficiency receptor-mediated delivery of small and large (48 kilobase) gene constructs using the endosome disruption activity of defective or inactivated adenovirus particles," *Proc. Natl. Acad. Sci. USA,* 89:6094–6098, 1992.
Coxson et al., *Biotropica,* 24:121–133, 1992.
Cuozzo et al., *Bio/Technology,* 6:549–553, 1988.
Curiel, "Gene transfer mediated by adenovirus-polylysine DNA complexes," *In: Viruses in Human Gene Therapy,* J.-M. H. Vos (Ed.), Carolina Academic Press, Durham, NC, pp 179–212,1994.
Cutler et al., *J. Plant Physiol.,* 135:351–354, 1989.
Czapla and Lang, *J. Econ. Entomol.,* 83:2480–2485, 1990.
Davies et al., *Plant Physiol.,* 93:588–595, 1990.
De Jager R. et al., "Current status of cancer immunodetection with radiolabeled human monoclonal antibodies" *Semin Nucl Med* 23(2):165–179, 1993.
Dellaporta et al., *In: Chromosome Structure and Function: Impact of New Concepts,* 18th Stadler Genetics Symposium, 11:263–282, 1988.
Depicker et al., *Plant Cell Reports,* 7:63–66, 1988.
D'Halluin et al., "Transgenic maize plants by tissue electroporation," *Plant Cell,* 4(12):1495–1505, 1992.
Dholakia et al., *J. Biol. Chem.,* 264, 20638–20642, 1989.
Doolittle M H and Ben-Zeev O, "Immunodetection of lipoprotein lipase: antibody production, immunoprecipitation, and western blotting techniques" *Methods Mol Biol.,* 109:215–237, 1999.
Dure et al., *Plant Molecular Biology,* 12:475–486, 1989.
Erdmann et al., *Mol. Jour. Gen. Micro.,* 138:363–368, 1992.
Fechheimer et al., "Transfection of mammalian cells with plasmid DNA by scrape loading and sonication loading," *Proc. Natl. Acad. Sci. USA* 84:8463–8467, 1987.
Fisher et al., "Isolation and characterization of the human tissue-type plasminogen activator structural gene including the 5' flanking region," *J. Biol. Chem.,* 260:112223–11230, 1985.
Fitzpatrick, *Gen. Engineering News,* 22:7, 1993.
Forster and Symons, *Cell,* 49:211–220, 1987.
Fraley and Fornari Kaplan, "Entrapment of a bacterial plasmid in phospholipid vesicles:potential for gene transfer," *Proc. Nat'l. Acad. Sci. USA* 76:3348–3352, 1979.
Fromm et al., "Stable transformation of maize after gene transfer by electroporation," *Nature,* 319:791–793, 1986.
Fromm et al., *Nature,* 312:791–793, 1986.
Gatehouse et al., *J. Sci. Food. Agric.,* 35:373–380, 1984.
Gerlach et al., *Nature* 328:802–805, 1987.
Ghosh and Bachhawat, "Targeting of liposomes to hepatocytes," *In: Liver Diseases, Targeted Diagnosis and Therapy Using Specific Receptors and Ligands,* Wu and Wu (Eds.), Marcel Dekker, New York, pp 87–104, 1991.
Ghosh-Biswas et al., "Transgenic Indica rice (*Oryza sativa* L.) plants obtained by direct gene transfer to protoplasts," *J. Biotechnol.,* 32(1):1–10, 1994.
Gopal., "Gene transfer method for transient gene expression, stable transformation, and cotransformation of suspension cell cultures," *Mol. Cell. Biol.,* 5:1188–1190, 1985.
Goring et al., *Proc. Nat'l Acad. Sci. USA,* 88:1770–1774, 1991.
Graham and Van Der Eb, "A new technique for the assay of infectivity of human adenovirus 5 DNA," *Virology,* 52:456–467, 1973.
Guerrero et al., *Plant Molecular Biology,* 15:11–26, 1990.
Gulbis B and Galand P, "Inmunodetection of the p21-ras products in human normal and preneoplastic tissues and solid tumors: a review" *Hum Pathol* 24(12):1271–1285, 1993.
Gupta et al., *Proc. Nat'l Acad. Sci. USA,* 90:1629–1633, 1993.
Hagio et al., "Stable transformation of sorghum cell cultures after bombardment with DNA coated microprojectiles," *Plant Cell Rep.,* 10(5):260–264, 1991.
Hammock et al., *Nature,* 344:458–461, 1990.
Harland and Weintraub, "Translation of mRNA injected into *Xenopus oocytes* is specifically inhibited by antisense RNA," *J. Cell Biol.,* 101: 1094–1099, 1985.
Harlow and Lane, *In: Antibodies: A laboratory Manual.,* Cold Spring Harbor Laboratories, Cold Spring Harbor, N.Y., 1988.
Haseloff and Gerlach, *Nature,* 334:585–591, 1988.
He et al., *Plant Cell Reports,* 14 (2–3):192–196, 1994.
Hemenway et al., *The EMBO J.,* 7:1273–1280, 1988.
Hensgens et al., "Transient and stable expression of gusA fusions with rice genes in rice, barley and perennial ryegrass," *Plant Mol. Biol.,* 22(6):1101–1127, 1993.
Hiei et al., "Transformation of rice mediated by agrobacterium tumefaciens," *Plant Mol. Biol.,* 35(1–2):205–218, 1997.
Hilder et al., *Nature,* 330:160–163, 1987.
Hou and Lin, *Plant Physiology,* 111:166, 1996.
Ikeda et al., *J. Bacteriol.,* 169:5615–5621, 1987.
Ishida et al., "High efficiency transformation of maize (Zea mays L.) mediated by *Agrobacterium tumefaciens,*" *Nat Biotechnol.,* 14:745–50, 1996.
Joyce, *Nature,* 338:217–244, 1989.
Kaasen et al., *J. Bacteriology,* 174:889–898, 1992.
Kaeppler et al., "Silicon carbide fiber-mediated stable transformation of plant cells," *Theor. Appl. Genet.,* 84(5–6):560–566, 1992.
Kaeppler et al., *Plant Cell Reports* 9: 415–418, 1990.
Kaneda et al., "Increased expression of DNA cointroduced with nuclear protein in adult rat liver," *Science,* 243:375–378, 1989.
Kang et al., *Science,* 240:1034–1036, 1988.
Karsten et al., *Botanica Marina,* 35:11–19, 1992.
Kato et al., "Expression of hepatitis β virus surface antigen in adult rat liver," *J. Biol. Chem.,* 266:3361–3364, 1991.
Kelleher and Vos, "Long-term episomal gene delivery in human lymphoid cells using human and avian adenoviral-assisted transfection," *Biotechniques,* 17(6):1110–1117, 1994.
Khatoon et al., Ann. of Neurology, 26, 210–219, 1989.
Kim and Cech, *Proc. Nat'l Acad. Sci. USA,* 84:8788–8792, 1987.
King et al., J. Biol. Chem., 269, 10210–10218, 1989.
Klee et al., *Bio-Technology,* 3(7):637–642, 1985.
Knittel et al., *Plant Cell Reports,* 14(2–3):81–86, 1994.
Kohler et al., Methods Enzymol., 178:3, 1989.
Koster and Leopold, *Plant Physiol.,* 88:829–832, 1988.
Kreier et al., Infection, Resistance and Immunity, Harper & Row, New York, (1991)).
Laqueyrerie et al., "Cloning, sequencing, and expression of the apa gene coding for the Mycobacterium tuberculosis 45/47-kilodalton secreted antigen complex," *Infection and Immunity,* 63:4003–4010, 1995.
Lazzeri, "Stable transformation of barley via direct DNA uptake. Electroporation- and PEG-mediated protoplast transformation," *Methods Mol. Biol.,* 49:95–106, 1995.
Lee and Saier, *J. of Bacteriol.,* 153–685, 1983.

Lee et al., *Korean J. Genet.,* 11(2):65–72, 1989.
Lenert et al., *Science,* 248:1639–1643, 1990.
Levings, *Science,* 250:942–947, 1990.
Lieber and Strauss, *Mol. Cell. Biol.,* 15: 540–551, 1995.
Long et al., "Complete sequence of the cDNA for human alpha 1-antitrypsin and the gene for the S variant," *Biochemstry,* 23:4828–4837, 1984.
Loomis et al., *J. Expt. Zoology,* 252:9–15, 1989.
Lorz et al., *Mol Gen Genet,* 199:178–182, 1985.
Maas et al., "Preparation and transformation of monocot protoplasts," *Methods Cell Biol.,* 50:383–399, 1995.
Marcotte et al., *Nature,* 335:454, 1988.
Mariani et al., *Nature,* 347:737–741, 1990.
McCabe and Martinell, *Bio-Technology,* 11(5):596–598, 1993.
McCormac et al., *Euphytica,* v. 99 (1) p. 17–25: 1998.
Michel and Westhof, *J. Mol. Biol.,* 216:585–610, 1990.
Mundy and Chua, *The EMBO J.,* 7:2279–2286, 1988.
Murdock et al., *Phytochemistry,* 29:85–89, 1990.
Nagatani et al., "DNA delivery into rice cells and transformation using silicon carbide whiskers," *Biotech. Tech.,* 11(7):471–473, 1997.
Nakamura et al., 1987.
Napoli et al., *Plant Cell,* 2:279–289, 1990.
Nicolau and Sene, "Liposome-mediated DNA transfer in eukaryotic cells: dependence of the transfer efficiency upon the type of liposomes used and the host cell cycle stage," *Biochem. Biophys. Acta,* 721:185–190, 1982.
Nicolau et al., "Liposomes as carriers for in vivo gene transfer and expression," *Methods Enzymol.,* 149:157–176, 1987.
Nisson et al., "Rapid and efficient cloning of Alu-PCR products using uracil DNA glycosylase," PCR® *Methods and Applications,* 1: 120–123, 1991.
Omirulleh et al., "Activity of a chimeric promoter with the doubled CaMV 35S enhancer element in protoplast-derived cells and transgenic plants in maize." *Plant Mol. Biol.,* 21:415–28, 1993.
O'Shannessy et al., *J. Immun. Meth.,* 99, 153–161, 1987.
Owens & Haley, *J. Biol. Chem.,* 259:14843–14848, 1987.
Palukaitis et al., *Virology,* 99:145–151, 1979.
PCT Application WO 92/17598
PCT Application WO 94/09699
PCT Application WO 95/06128
Perales et al., "Gene transfer in vivo: sustained expression and regulation of genes introduced into the liver by receptor-targeted uptake," *Proc. Natl. Acad. Sci. USA,* 91:4086–4090, 1994.
Perlak et al., *Proc. Nat'l Acad. Sci. USA,* 88:3324–3328, 1991.
Perriman et al., *Gene,* 113:157–163, 1992.
Phi-Van et al., *Mol. Cell. Biol.,* 10:2302–2307, 1990.
Piatkowski et al., *Plant Physiol.,* 94:1682–1688, 1990.
Potrykus et al., *Mol. Gen. Genet.,* 199:183–188, 1985.
Potter & Haley, *Meth. in Enzymol.,* 91, 613–633, 1983.
Potter et al., "Enhancer-dependent expression of human k immunoglobulin genes introduced into mouse pre-B lymphocytes by electroporation," *Proc. Natl Acad. Sci. USA,* 81:7161–7165, 1984.
Prody et al., *Science,* 231:1577–1580, 1986.
Reed et al., *J. Gen. Microbiology,* 130:1–4, 1984.
Reinhold-Hurek and Shub, *Nature,* 357:173–176, 1992.
Rensburg et al., *J. Plant Physiol.,* 141:188–194, 1993.
Rhodes et al., "Transformation of maize by electroporation of embryos," *Methods Mol. Biol.,* 55:121–131, 1995.
Rippe et al., "DNA-mediated gene transfer into adult rat hepatocytes in primary culture," *Mol. Cell Biol.,* 10:689–695, 1990.
Ritala et al., "Fertile transgenic barley to particle bombardment of immature embryos," *Plant Mol. Biol.,* 24(2):317–325, 1994.
Rogers et al., *Methods Enzymol.,* 153:253–277, 1987.
Sambrook et al., In: *Molecular Cloning: A Laboratory Manual,* Vol. 1, Cold Spring Harbor Laboratory Press, Cold Spring Harbor, N.Y., Ch. 7,7.19–17.29, 1989.
Sanford et al., "An improved, helium-driven biolistic device," *Technique J. Methods Cell Molec. Biol.,* 3:3–16, 1991.
Sasso et al., *J. Immunol.,* 142:2778–2783, 1989.
Sato et al., "Immunostimulatory DNA sequences necessary for effective intradermal gene immunization," *Science,* 273:352–354, 1996.
Shagan and Bar-Zvi, *Plant Physiol.,* 101:1397–1398, 1993.
Shapiro, In: *Mobile Genetic Elements,* 1983.
Shimoni et al., "A recombinant protein of two high molelcular weight glutenins alters gluten polymer formation in transgenic wheat," *J. Biol. Chem.,* 272:15488–15495, 1997.
Shorki et al., *J. Immunol.,* 146:936–940, 1991.
Silvermann et al., *J. Clin. Invest.,* 96:417–426, 1995.
Singsit et al., "Expression of a Bacillus thuringiensis cryIA (c) gene in transgenic peanut plants and its efficacy against lesser cornstalk borer," *Transgenic Res.,* 6:169–76, 1997.
Smith et al., *Mol. Gen. Genet.,* 224:447–481, 1990.
Stemmer et al., *Gene,* 164:49–53, 1995.
Stougaard, *The Plant Journal.,* 3:755–761, 1993.
Takumi and Shimada, "Variation in transformation frequencies among six common wheat cultivars through particle bombardment of scutellar tissues," *Genes Genet. Sys.,* 72:63–69, 1997.
Tang et al., "Genetic immunization is a simple method for eliciting an immune response," *Nature,* 356:152–154, 1992.
Tarczynski et al., *Proc. Nat'l Acad. Sci. USA,* 89:1–5, 1992.
Tarczynski et al., *Science,* 259:508–510, 1993.
Thillet et al., *J. Biol. Chem.,* 263:12500–12508, 1988.
Thompson et al., "Maize transformation utilizing silicon carbide whiskers: A review," *Euphytica,* 85(1–3):75–80, 1995.
Thompson et al., *Euphytica,* 85(1–3):75–80, 1995.
Tingay et al., *The Plant Journal* v. 11 (6) p. 1369–1376. 1997.
Tomes et al., "Transgenic tobacco plants and their progeny derived by microprojectile bombardment of tobacco leaves," *Plant Mol. Biol.,* 14:261–8, 1990
Torbet et al., "Transformation of oat using mature embryo-derived tissue cultures," *Crop Science,* 38:226–231, 1998.
Torbet et al., "Use of paromomycin as a selective agent for oat transformation," *Plant Cell Reports,* 14:635–640, 1995.
Toriyama et al., *Theor Appl. Genet.,* 73:16, 1986.
Tsukada et al., *Plant Cell Physiol.,* 30(4)599–604, 1989.
Tur-Kaspa et al., "Use of electroporation to introduce biologically active foreign genes into primary rat hepatocytes," *Mol. Cell Biol.,* 6:716–718, 1986.
U.S. Pat. No. 5,354,855
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509

U.S. Pat. No. 4,938,948
U.S. Pat. No. 5,021,236
U.S. Pat. No. 5,168,053
U.S. Pat. No. 5,196,066
U.S. Pat. No. 5,268,526
U.S. Pat. No. 5,302,523
U.S. Pat. No. 5,322,783
U.S. Pat. No. 5,384,253
U.S. Pat. No. 5,464,765
U.S. Pat. No. 5,500,365
U.S. Pat. No. 5,508,184
U.S. Pat. No. 5,538,877
U.S. Pat. No. 5,538,880
U.S. Pat. No. 5,550,318
U.S. Pat. No. 5,563,055
U.S. Pat. No. 5,591,616
U.S. Pat. No. 5,610,042
U.S. Pat. No. 5,624,824
U.S. Pat. No. 5,625,047
U.S. Pat. No. 5,689,052
U.S. Pat. No. 5,780,709
U.S. Pat. No. 6,040,497
Uchimiya et al., *Mol. Gen. Genet.*, 204:204, 1986.
Van der Krol et al., *Plant Cell*, 2:291–99, 1990.
Van Eck et al., *Plant Cell Reports*, 14(5):299–304, 1995.
Vasil et al., *Plant Physiol.*, 91:1575–1579, 1989.
Vernon and Bohnert, *The EMBO J.*, 11:2077–2085, 1992.
Wagner et al., *Science*, 260:1510–1513, 1990.
Watrud et al., In: *Engineered Organisms and the Environment*, 1985.
Williams, Johnston, Riedy, DeVitt, McElligott, Sanford, "Direct transformation of skin and liver tissue in the living mouse," *Proc. Natl. Acad., USA*, 88:2726–2730, 1991.
Wolff et al., "Direct gene transfer into mouse muscle in vivo," *Science*, 246:1464–1468, 1990.
Wolter et al., *The EMBO J.*, 4685–4692, 1992.
Wong et al., "Appearance of β-lactamase activity in animal cells upon liposome mediated gene transfer," *Gene*, 10:87–94, 1980.
Wu and Wu, "Receptor-mediated in vitro gene transfections by a soluble DNA carrier system," *J. Biol. Chem.*, 262:4429–4432, 1987.
Wu and Wu, *Adv. Drug Delivery Rev.*, 12:159–167, 1993.
Xiang and Guerra, *Plant Physiol.*, 102:287–293, 1993.
Xie et al., "Study of Mechanisms of Electric Field-Induced DNA Transfection V. Effects of DNA Topology on Surface Binding, Cell Uptake, Expression, and Integration into Host Chromosomes of DNA in the Mammalian Cell," *Biophysical Journal*, 65:1684–1689, 1993.
Xu et al., *Plant Physiol.*, 110:249–257, 1996.
Yamada et al., *Plant Cell Rep.*, 4:85, 1986.
Yamaguchi-Shinozaki et al., *Plant Cell Physiol.*, 33:217–224, 1992.
Yuan and Altman, *Science*, 263:1269–1273, 1994.
Yuan et al., *Proc. Nat'l Acad. Sci. USA*, 89:8006–8010, 1992.
Zhang et al., "Agrobacterium-mediated transformation of elite indica and japonica rice cultivars," *Mol. Biotechnol.*, 8(3):223–231, 1997.
Zheng and Edwards, "Expression of resistance to barley stripe mosaic virus in barley and oat protoplasts," *J. Gen. Virol.*, 71:1865–1868, 1990.
Zhou et al., *Plant Cell Reports*, 12(11).612–616, 1993.

What is claimed is:

1. A method of screening at least one open reading frame to determine whether it encodes a polypeptide with an ability to generate an immune response in an animal, comprising:
   a) preparing in vitro at least one linear or circular expression element comprising an open reading frame linked to a promoter;
   b) introducing the at least one linear or circular expression element into a cell within an animal without intervening cloning or bacterial propagation; and
   c) assaying to determine whether an immune response is generated in the animal by expression of a polypeptide encoded by the open reading frame in the expression element.

2. The method of claim 1, wherein the linear or circular expression element is injected into the animal.

3. The method of claim 1, wherein the linear or circular expression element further comprises a terminator linked to the open reading frame.

4. The method of claim 1, wherein the open reading frame is from a pathogen genomic sequence.

5. The method of claim 1, wherein preparing the expression element comprises non-covalently linking the promoter to the open reading frame.

6. The method of claim 1, wherein preparation of the expression element comprises polymerase chain reaction.

7. The method of claim 1, wherein preparing the expression element comprises chemical synthesis of the open reading frame.

8. The method of claim 1, further comprising identifying an antibody produced by the animal and directed against the polypeptide encoded by the open reading frame.

9. The method of claim 4, wherein the pathogen is a virus, bacterium, fungus, alga, protozoan, arthropod, nematode, platyhelminthe, or plant.

10. The method of claim 4, further comprising testing an animal comprising the cell by challenge with the pathogen.

11. The method of claim 5, wherein preparing the expression element further comprises non-covalently linking a terminator to the open reading frame.

12. The method of claim 5, wherein the open reading frame is produced in vivo and then non-covalently linked to the promoter in vitro.

13. The method of claim 6, wherein preparation of the expression element comprises polymerase chain reaction to produce the open reading frame.

14. The method of claim 8, further comprising isolating the antibody.

15. The method of claim 10, wherein the animal is protected from the challenge with the pathogen.

16. The method of claim 15, further comprising identifying one or more antigens conferring protection to the animal.

17. A method of screening at least one open reading frame to determine whether it encodes a polypeptide with an ability to generate an immune response in an animal,
   a) preparing in vitro at least one linear or circular expression element by non-covalently linking an open reading frame to a promoter;
   b) introducing the at least one linear or circular expression element into a cell within an animal without intervening cloning or bacterial propagation;
   c) assaying to determine whether an immune response is generated in the animal by expression of a polypeptide encoded by the open reading frame in the expression element.

18. The method of claim 17, wherein preparing the linear or circular expression element further comprises non-covalently linking a terminator to the open reading frame.

19. The method of claim 17, wherein the open reading frame is from a pathogen genomic sequence.

20. The method of claim 17, wherein the open reading frame is produced in vivo and then non-covalently linked to the promoter in vitro.

21. The method of claim 17, wherein preparation of the expression element comprises polymerase chain reaction.

22. The method of claim 17, wherein preparing the expression element comprises chemical synthesis of the open reading frame.

23. The method of claim 17, further comprising identifying an antibody produced by the animal and directed against the polypeptide encoded by the open reading frame.

24. The method of claim 19, further comprising testing an animal comprising the cell by challenge with the pathogen.

25. The method of claim 21, wherein preparation of the expression element comprises polymerase chain reaction to produce the open reading frame.

26. The method of claim 23, further comprising isolating the antibody.

27. The method of claim 24, wherein the animal is protected from the challenge with the pathogen.

28. The method of claim 27, further comprising identifying one or more antigens conferring protection to the animal.

* * * * *

UNITED STATES PATENT AND TRADEMARK OFFICE
CERTIFICATE OF CORRECTION

PATENT NO.    : 6,410,241 B1
DATED         : June 25, 2002
INVENTOR(S)   : Sykes et al.

It is certified that error appears in the above-identified patent and that said Letters Patent is hereby corrected as shown below:

<u>Column 68,</u>
Line 50, after "animal,", please insert -- comprising: --.
Line 57, after "propagation;", please insert -- and --.

Signed and Sealed this

Nineteenth Day of November, 2002

Attest:

JAMES E. ROGAN
Attesting Officer          Director of the United States Patent and Trademark Office